(12) United States Patent
Jeschke et al.

(10) Patent No.: US 8,796,175 B2
(45) Date of Patent: Aug. 5, 2014

(54) METHOD FOR ENHANCING PLANT INTRINSIC DEFENSE

(75) Inventors: Peter Jeschke, Bergisch Gladbach (DE); Wolfgang Thielert, Odenthal (DE); Heike Hungenberg, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 48 days.

(21) Appl. No.: 13/061,360

(22) PCT Filed: Aug. 17, 2009

(86) PCT No.: PCT/EP2009/006064
§ 371 (c)(1),
(2), (4) Date: Feb. 28, 2011

(87) PCT Pub. No.: WO2010/022897
PCT Pub. Date: Mar. 4, 2010

(65) Prior Publication Data
US 2011/0160061 A1   Jun. 30, 2011

(30) Foreign Application Priority Data
Aug. 29, 2008 (DE) .......................... 10 2008 041 695

(51) Int. Cl.
| | |
|---|---|
| *A01N 25/26* | (2006.01) |
| *A01N 59/04* | (2006.01) |
| *A01N 43/40* | (2006.01) |
| *A01N 43/78* | (2006.01) |
| *A01N 33/00* | (2006.01) |
| *A01N 41/02* | (2006.01) |
| *A01N 63/00* | (2006.01) |
| *A61K 31/44* | (2006.01) |
| *C12N 15/82* | (2006.01) |
| *C07C 291/00* | (2006.01) |
| *C07C 261/00* | (2006.01) |
| *C07C 313/00* | (2006.01) |
| *C07C 249/00* | (2006.01) |

(52) U.S. Cl.
USPC .......... 504/100; 504/101; 504/118; 504/189; 504/244; 504/266; 504/326; 504/350; 435/468; 514/336; 514/357; 558/299; 564/102; 564/103; 564/229; 564/297; 546/313; 546/329; 546/330

(58) Field of Classification Search
USPC ......... 504/100, 101, 118, 189, 244, 266, 326, 504/350; 435/468; 558/299; 564/102, 103, 564/229, 297; 514/336, 357
See application file for complete search history.

(56) References Cited

U.S. PATENT DOCUMENTS

| | | |
|---|---|---|
| 4,245,432 A | 1/1981 | Dannelly |
| 4,272,417 A | 6/1981 | Barke et al. |

(Continued)

FOREIGN PATENT DOCUMENTS

| | | |
|---|---|---|
| CA | 2 671 179 A1 | 6/2008 |
| DE | 41 28 828 A1 | 3/1993 |

(Continued)

OTHER PUBLICATIONS

Skopelitis et al., "Abiotic Stress Generates ROS That Signal Expressionn of Anionic Glutamate Dehydrogenases to Form Glutamate for Proline Synthesis in Tobacco and Grapevine," 2006, The Plant Cell, 18:2767-2781.*

(Continued)

*Primary Examiner* — Jane C Oswecki
(74) *Attorney, Agent, or Firm* — Sterne, Kessler, Goldstein & Fox P.L.L.C.

(57) ABSTRACT

The invention relates to the use of at least one compound selected from the class of the sulphoximines for enhancing plants' intrinsic defenses and/or for improving plant growth and/or for enhancing the resistance of plants to plant diseases which are caused by fungi, bacteria, viruses, MLOs (mycoplasma-like organisms) and/or RLOs (rickettsia-like organisms), and/or for enhancing the resistance of plants to abiotic stress factors.

17 Claims, 3 Drawing Sheets

(56) References Cited

U.S. PATENT DOCUMENTS

| | | |
|---|---|---|
| 4,761,373 A | 8/1988 | Anderson et al. |
| 4,808,430 A | 2/1989 | Kouno |
| 4,931,581 A | 6/1990 | Schurter et al. |
| 5,013,659 A | 5/1991 | Bedbrook et al. |
| 5,084,082 A | 1/1992 | Sebastian |
| 5,141,870 A | 8/1992 | Bedbrook et al. |
| 5,198,599 A | 3/1993 | Thill |
| 5,273,894 A | 12/1993 | Strauch et al. |
| 5,276,268 A | 1/1994 | Strauch et al. |
| 5,304,732 A | 4/1994 | Anderson et al. |
| 5,331,107 A | 7/1994 | Anderson et al. |
| 5,378,824 A | 1/1995 | Bedbrook et al. |
| 5,434,283 A | 7/1995 | Wong et al. |
| 5,463,175 A | 10/1995 | Barry et al. |
| 5,561,236 A | 10/1996 | Leemans et al. |
| 5,605,011 A | 2/1997 | Bedbrook et al. |
| 5,637,489 A | 6/1997 | Strauch et al. |
| 5,646,024 A | 7/1997 | Leemans et al. |
| 5,648,477 A | 7/1997 | Leemans et al. |
| 5,712,107 A | 1/1998 | Nichols |
| 5,731,180 A | 3/1998 | Dietrich |
| 5,739,082 A | 4/1998 | Donn |
| 5,767,361 A | 6/1998 | Dietrich |
| 5,773,702 A | 6/1998 | Penner et al. |
| 5,776,760 A | 7/1998 | Barry et al. |
| 5,789,566 A | 8/1998 | Bonhomme et al. |
| 5,824,790 A | 10/1998 | Keeling et al. |
| 5,840,946 A | 11/1998 | Wong et al. |
| 5,866,782 A | 2/1999 | Iwabuchi et al. |
| 5,876,739 A | 3/1999 | Turnblad et al. |
| 5,908,810 A | 6/1999 | Donn |
| 5,908,975 A | 6/1999 | Caimi et al. |
| 5,928,937 A | 7/1999 | Kakefuda et al. |
| 5,965,755 A | 10/1999 | Sernyk et al. |
| 5,969,169 A | 10/1999 | Fan |
| 6,013,861 A | 1/2000 | Bird et al. |
| 6,063,947 A | 5/2000 | DeBonte et al. |
| 6,130,367 A | 10/2000 | Kossmann et al. |
| 6,139,596 A | 10/2000 | Barth et al. |
| 6,162,966 A | 12/2000 | Kossmann et al. |
| 6,169,190 B1 | 1/2001 | Lanuza et al. |
| 6,207,880 B1 | 3/2001 | Kossmann et al. |
| 6,211,436 B1 | 4/2001 | Kossmann et al. |
| 6,229,072 B1 | 5/2001 | Burns et al. |
| 6,245,968 B1 | 6/2001 | Boudec et al. |
| 6,255,561 B1 | 7/2001 | Kossmann et al. |
| 6,255,563 B1 | 7/2001 | Emmermann et al. |
| 6,268,549 B1 | 7/2001 | Sailland et al. |
| 6,270,828 B1 | 8/2001 | DeBonte et al. |
| 6,284,479 B1 | 9/2001 | Nichols |
| 6,307,124 B1 | 10/2001 | Kossmann et al. |
| 6,307,125 B1 | 10/2001 | Block et al. |
| 6,323,392 B1 | 11/2001 | Charne |
| 6,515,203 B1 | 2/2003 | Heyer et al. |
| 6,566,587 B1 | 5/2003 | Lebrun et al. |
| 6,570,065 B1 | 5/2003 | Kossmann et al. |
| 6,590,141 B1 | 7/2003 | Frohberg |
| 6,596,928 B1 | 7/2003 | Landschütze |
| 6,699,694 B1 | 3/2004 | Buttcher et al. |
| 6,734,341 B2 | 5/2004 | Singletary et al. |
| 6,791,010 B1 | 9/2004 | Frohberg |
| 6,812,010 B1 | 11/2004 | Derose et al. |
| 6,890,732 B1 | 5/2005 | Loerz et al. |
| 6,891,088 B1 | 5/2005 | Neuhaus et al. |
| 6,951,969 B1 | 10/2005 | Loerz et al. |
| 7,112,665 B1 | 9/2006 | Leemans et al. |
| 7,612,018 B2 * | 11/2009 | Jeanguenat et al. .......... 504/326 |
| 2002/0031826 A1 | 3/2002 | Nichols |
| 2003/0069242 A1 | 4/2003 | Toriyabe et al. |
| 2003/0176428 A1 | 9/2003 | Schneidersmann et al. |
| 2004/0073966 A1 | 4/2004 | Zink et al. |
| 2005/0228027 A1 | 10/2005 | Zhu et al. |
| 2005/0257283 A1 | 11/2005 | Matringe et al. |
| 2006/0015966 A1 | 1/2006 | Landschutze |
| 2006/0168690 A1 | 7/2006 | Shibatani et al. |
| 2007/0299264 A1 * | 12/2007 | Huang et al. ................ 546/281.4 |
| 2008/0132413 A1 | 6/2008 | Deall et al. |
| 2008/0250533 A1 | 10/2008 | Frohberg |
| 2009/0018019 A1 | 1/2009 | Thielert et al. |
| 2009/0023782 A1 * | 1/2009 | Babcock ........................ 514/336 |
| 2009/0105235 A1 | 4/2009 | Jeschke et al. |
| 2009/0247551 A1 | 10/2009 | Jeschke et al. |
| 2009/0253749 A1 | 10/2009 | Jeschke et al. |
| 2009/0298888 A1 * | 12/2009 | Thielert et al. ................ 514/341 |
| 2009/0317535 A1 | 12/2009 | Frohberg et al. |
| 2010/0034953 A1 | 2/2010 | Frohberg |
| 2010/0240705 A1 | 9/2010 | Jeschke et al. |

FOREIGN PATENT DOCUMENTS

| | | |
|---|---|---|
| EP | 0 539 588 A1 | 5/1993 |
| EP | 0 571 427 B1 | 12/1993 |
| EP | 0 663 956 B1 | 7/1995 |
| EP | 0 719 338 B1 | 7/1996 |
| EP | 0 719 213 B1 | 8/1996 |
| EP | 1 731 037 A1 | 12/2006 |
| GB | 1 292 718 | 10/1972 |
| JP | 2006-304779 A | 11/2006 |
| WO | WO 91/02069 A1 | 2/1991 |
| WO | WO 94/04693 A2 | 3/1994 |
| WO | WO 94/09144 A1 | 4/1994 |
| WO | WO 94/11520 A2 | 5/1994 |
| WO | WO 94/21795 A1 | 9/1994 |
| WO | WO 95/04826 A1 | 2/1995 |
| WO | WO 95/26407 A1 | 10/1995 |
| WO | WO 95/31553 A1 | 11/1995 |
| WO | WO 95/35026 A1 | 12/1995 |
| WO | WO 96/01904 A1 | 1/1996 |
| WO | WO 96/19581 A1 | 6/1996 |
| WO | WO 96/21023 A1 | 7/1996 |
| WO | WO 96/33270 A1 | 10/1996 |
| WO | WO 96/34968 A2 | 11/1996 |
| WO | WO 97/20936 A1 | 6/1997 |
| WO | WO 97/41218 A1 | 11/1997 |
| WO | WO 97/47806 A1 | 12/1997 |
| WO | WO 97/47807 A1 | 12/1997 |
| WO | WO 97/47808 A1 | 12/1997 |
| WO | WO 98/00549 A1 | 1/1998 |
| WO | WO 98/20145 A2 | 5/1998 |
| WO | WO 98/22604 A1 | 5/1998 |
| WO | WO 98/27212 A1 | 6/1998 |
| WO | WO 98/27806 A1 | 7/1998 |
| WO | WO 98/32326 A2 | 7/1998 |
| WO | WO 98/40503 A1 | 9/1998 |
| WO | WO 99/12950 A2 | 3/1999 |
| WO | WO 99/24593 A1 | 5/1999 |
| WO | WO 99/53072 A1 | 10/1999 |
| WO | WO 99/57965 A1 | 11/1999 |
| WO | WO 99/66050 A1 | 12/1999 |
| WO | WO 00/04173 A1 | 1/2000 |
| WO | WO 00/11192 A2 | 3/2000 |
| WO | WO 00/14249 A1 | 3/2000 |
| WO | WO 00/28052 A2 | 5/2000 |
| WO | WO 00/66747 A1 | 11/2000 |
| WO | WO 00/73422 A1 | 12/2000 |
| WO | WO 00/77229 A2 | 12/2000 |
| WO | WO 01/14569 A2 | 3/2001 |
| WO | WO 01/17333 A1 | 3/2001 |
| WO | WO 01/19975 A2 | 3/2001 |
| WO | WO 01/24615 A1 | 4/2001 |
| WO | WO 01/65922 A2 | 9/2001 |
| WO | WO 01/66704 A2 | 9/2001 |
| WO | WO 01/98509 A2 | 12/2001 |
| WO | WO 02/26995 A1 | 4/2002 |
| WO | WO 02/28186 A2 | 4/2002 |
| WO | WO 02/34923 A2 | 5/2002 |
| WO | WO 02/36782 A2 | 5/2002 |
| WO | WO 02/45485 A1 | 6/2002 |
| WO | WO 02/79410 A2 | 10/2002 |
| WO | WO 02/80675 A1 | 10/2002 |
| WO | WO 02/101059 A2 | 12/2002 |
| WO | WO 03/013226 A2 | 2/2003 |
| WO | WO 03/033540 A2 | 4/2003 |
| WO | WO 03/092360 A2 | 11/2003 |

(56) References Cited

FOREIGN PATENT DOCUMENTS

| | | |
|---|---|---|
| WO | WO 2004/040012 A2 | 5/2004 |
| WO | WO 2004/053219 A2 | 6/2004 |
| WO | WO 2004/056999 A1 | 7/2004 |
| WO | WO 2004/078983 A2 | 9/2004 |
| WO | WO 2004/090140 A2 | 10/2004 |
| WO | WO 2004/106529 A2 | 12/2004 |
| WO | WO 2005/002359 A2 | 1/2005 |
| WO | WO 2005/023324 A2 | 1/2005 |
| WO | WO 2005/012515 A2 | 2/2005 |
| WO | WO 2005/017157 A1 | 2/2005 |
| WO | WO 2005/020673 A1 | 3/2005 |
| WO | WO2005027632 A2 * | 3/2005 |
| WO | WO 2005/030941 A1 | 4/2005 |
| WO | WO 2005/030942 A1 | 4/2005 |
| WO | WO 2005/093093 A2 | 10/2005 |
| WO | WO 2005/095617 A2 | 10/2005 |
| WO | WO 2005/095618 A2 | 10/2005 |
| WO | WO 2005/095619 A1 | 10/2005 |
| WO | WO 2005/095632 A2 | 10/2005 |
| WO | WO 2005/123927 A1 | 12/2005 |
| WO | WO 2006/007373 A2 | 1/2006 |
| WO | WO 2006/015376 A2 | 2/2006 |
| WO | WO 2006/018319 A1 | 2/2006 |
| WO | WO 2006/021972 A1 | 3/2006 |
| WO | WO 2006/024351 A1 | 3/2006 |
| WO | WO 2006/032538 A1 | 3/2006 |
| WO | WO 2006/060029 A2 | 6/2006 |
| WO | WO 2006/060634 A2 | 6/2006 |
| WO | WO 2006/063862 A1 | 6/2006 |
| WO | WO 2006/072603 A2 | 7/2006 |
| WO | WO 2006/103107 A1 | 10/2006 |
| WO | WO 2006/108702 A1 | 10/2006 |
| WO | WO 2006/122662 A1 | 11/2006 |
| WO | WO 2006/133827 A2 | 12/2006 |
| WO | WO 2006/136351 A2 | 12/2006 |
| WO | WO 2007/009823 A1 | 1/2007 |
| WO | WO 2007/024782 A2 | 3/2007 |
| WO | WO 2007/027777 A2 | 3/2007 |
| WO | WO 2007/039314 A2 | 4/2007 |
| WO | WO 2007/039316 A1 | 4/2007 |
| WO | WO 2007/095229 A2 | 8/2007 |
| WO | WO 2007/149134 A1 | 12/2007 |
| WO | WO 2008/027073 A1 | 3/2008 |
| WO | WO 2008/027539 A1 | 3/2008 |
| WO | WO 2008/097235 A1 | 8/2008 |
| WO | WO 2009/134224 A1 | 11/2009 |

OTHER PUBLICATIONS

Achuo, E.A., et al., "The salicylic acid-dependent defence pathway is effective against different pathogens in tomato and tobacco," *Plant Pathology* 53:65-72, John Wiley & Sons, New York, USA (2004).

Barry, G., et al., "Inhibitors of Amino Acid Biosynthesis: Strategies for Imparting Glyphosate Tolerance to Crop Plants," *Current Topics in Plant Physiology* 7:139-145, American Society of Plant Physiologists, USA (1992).

Brown, R.S., et al., "Efficacy of Foliar Applications of Trimax Insecticide During Water-Deficit Stress on the Physiology and Yield of Cotton," *2004 Beltwide Cotton Conferences*, Texas 2231-2237, Bayer Business Services GmbH S&T-IC-LS Library Services Berlin, Germany (2004).

Comai, L., et al., "An Altered aroA Gene Product Confers Resistance to the Herbicide Glyphosate," *Science* 221:370-371, HighWire Press, USA (1983).

Crickmore, N., et al., "Revision of the Nomenclature for the *Bacillus thuringiensis* Pesticidal Crystal Proteins," *Microbiology and Molecular Biology Reviews* 62(3):807-813, American Society of Microbiology, USA (1998).

Crozier, A., et al., "Biosynthesis of Hormones and Elicitor Molecules," *Biochemistry & Molecular Biology of Plants* :850-929, American Society of Plant Physiologists, USA (2002).

Dangl, J.L. & Jones, J.D.G., "Plant pathogens and integrated defence responses to infection," *Nature* 411: 826-833, Macmillan Magazines Ltd., United States (2001).

Draber, W. and Wegler, R. "Gibberelline," *Chemie der Pflanzenschutz-und Schädlingsbekämpfungsmittel* 2:401-412, Springer Verlag, Germany (1970).

English language translation of Darber, W. and Wegler, R., "Phytohormone: 2. Gibberelline", Chemie der Pflanzenschutz und Schädlingbekämpfungsmittel vol. 2:401-412, Springer, Germany (1970).

Francis, M.I., et al., "Soil application of imidacloprid and related SAR-inducing compounds produces effective and persistent control of citrus canker," *European Journal of Plant Pathology* 124(2):283-292, Springer, USA (2009).

Gasser, C.S., et al., "Structure, Expression, and Evolution of the 5-Enolpyruvylshikimate-3-phosphate Synthase Genes of Petunia and Tomato," *The Journal of Biological Chemistry* 263:4280-4289, The American Society for Biochemistry and Molecular Biology, Inc., USA (1988).

Gonias, E.D., et al., "Effect of Trimax Insecticide on the Physiology, Growth and Yield of Cotton," *2004 Beltwide Cotton Conferences*, Texas 2225-2229, Bayer Business Services GmbH S&T-IC-LS Library Services Berlin, Germany (2004).

Kessler, A. & Baldwin, I.T., "Plant Responses to Insect Herbivory: The Emerging Molecular Analysis," *Annu. Rev. Plant Biol.* 53:299-328, Annual Reviews, United States (2002).

Krewer, G., et al., "Imidacloprid Insecticide Slows Development of Pierce's Disease in Bunch Grapes," *Journal of Entomological Science* 37(1):101-112, John Wiley & Sons, UK (2002).

Leal, R.S., "The use of Confidor S in the float, a new tobacco seedlings production system in the south of Brazil," *Pflanzenschutz-Nachrichten Bayer* 54:337-352, Bayer CropScience, Germany (2001).

Moellenbeck, D.J., et al., "Insecticidal proteins from *Bacillus thuringiensis* protect corn from corn rootworms," *Nature Biotechnology* 19:668-672, Nature Publishing Group, New York, USA (2001).

Pappu, H.R., et al., "Effect of acibenzolar-S-methyl and imidacloprid on suppression of tomato spotted wilt *Tospovirus* in flue-cured Tobacco," *Crop Protection* 19(5):349-354, Elsevier Science Ltd., The Netherlands (2000).

Pennazio, S., "The Hypersensitive Reaction of Higher Plants to Viruses: A Molecular Approach," *New Microbiologica* 18(2):229-240, EDIMS, Pavia, Italy (1995).

Rudolph, R.D. and Rogers, W.D., "The efficacy of imidacloprid treatment for reduction in the severity of insect vectored virus diseases of tobacco," *Pflanzenschutz-Nachrichten Bayer* 54:311-336, Bayer CropScience, Germany (2001).

Ryals, J.A., et al., "Sytemic Acquired Resistance," *The Plant Cell* 8:1809-1819, American Society of Plant Physiologists, USA (1996).

Schnepf, H.E., et al., "Characterization of Cry34/Cry35 Binary Insecticidal Proteins from Diverse *Bacillus thuringiensis* Strain Collections," *Applied and Enviornmental Microbiology* 71(4):1765-1774, American Society of Microbiology, USA (2005).

Sembdner, G. and Parthier, B., "The Biochemistry and the Physiological and Molecular Actions of Jasmonates," *Annual Review of Plant Physiology and Plant Molecular Biology* 44:569-589, American Reviews Inc., USA (1993).

Shah, D.M., et al., "Engineering Herbicide Tolerance in Transgenic Plants," *Science* 223:478-481, HighWire Press, USA (1986).

Singh, S., et al., "Effect of Insecticides and Herbicides on Root Rot of Cotton Caused by *Rhizoctonia solani* Kühn," *Annals of Biology* 19(2):179-181, John Wiley & Sons, Inc., USA (2003).

Tamblyn, C.M., et al., "Extended summary SCI Pesticides Group Meeting: Systemic Acquired Resistance," *Pesticide Science* 55:676-677, Society of Chemical Industry, USA (1999).

Thielert, W., "A unique product: The story of the imidacloprid stress shield," *Pflanzenschutz-Nachrichten Bayer* 59:73-86, Bayer CropScience, Germany (2006).

Tranel, P.J. and Wright, T.R., "Resistance of weeds to ALS-inhibiting herbicides: what have we learned?," *Weed Science* 50(6):700-712, Weed Science Society of America, Kansas, USA (2002).

Ullmann's Encyclopedia of Industrial Chemistry, 5th Edition, vol. A 10, pp. 323-431, Verlagsgesellscaft, Weinheim (1987).

(56) References Cited

OTHER PUBLICATIONS

Walling, L.L.., "The Myriad Plant Responses to Herbivores," *Journal of Plant Growth Regulation* 19(2):195-216, Springer Verlag, New York, USA (2000).

International Search Report for International Application No. PCT/EP2009/006064, European Patent Office, Netherlands, mailed on Nov. 22, 2010.

English language Abstract of German Patent Publication No. DE 41 28 828 A1, European Patent Office, espacenet database—Worldwide, (1993).

English language Abstract of Japanese Patent Publication No. 2006-304779 A, Japanese Patent Office, Searching PAJ database—Worldwide, (2006).

English language Abstract of WIPO Patent Publication No. WO 99/57965 A1, European Patent Office, espacenet database—Worldwide, (1999).

English language Abstract of WIPO Patent Publication No. WO 01/14569 A2, European Patent Office, espacenet database—Worldwide, (2001).

* cited by examiner

METHOD FOR ENHANCING PLANT INTRINSIC DEFENSE

The invention relates to methods which, using sulphoximines, are suitable for enhancing plants' intrinsic defenses and/or for improving plant growth and/or for increasing the resistance of plants to plant diseases which are caused by fungi, bacteria, viruses, MLOs (mycoplasma-like organisms) and/or RLOs (rickettsia-like organisms).

It is known that plants react to natural stress conditions such as, for example, cold, heat, drought, wounding, pathogen attack (viruses, bacteria, fungi), insects and the like, but also to herbicides, with specific or unspecific defense mechanisms (Pflanzenbiochemie, p. 393-462, Spektrum Akademischer Verlag, Heidelberg, Berlin, Oxford, Hans W. Heldt, 1996.; Biochemistry and Molecular Biology of Plants, p. 1102-1203, American Society of Plant Physiologists, Rockville, Md., eds. Buchanan, Gruissem, Jones, 2000). In this context, signal substances, for example cell wall constituents which have been generated by wounding, or specific signal substances which originate from the pathogen, act as inductors of plant signal transduction chains which eventually lead to the formation of defence molecules directed against the stress factor. They can take the form of for example, (a) low-molecular weight substances such as, for example, phytoalexins, (b) nonenzymatic proteins such as, for example, pathogen-related proteins (PR proteins), (c) enzymatic proteins such as, for example, chitinases, glucanases, or (d) specific inhibitors of essential proteins such as, for example, protease inhibitors, xylanase inhibitors, which directly attack the pathogen or interfere with its proliferation (Dangl and Jones, Nature 411, 826-833, 2001; Kessler and Baldwin, Annual Review of Plant Biology, 53, 299-328, 2003).

An additional defence mechanism is what is known as the hypersensitive reaction (HR), which is mediated by oxidative stress and which leads to the death of plant tissue around an infection focus, thus preventing the spreading of plant pathogens which depend on live cells (Pennazio, New Microbiol. 18, 229-240, 1995).

In the further course of an infection, signals are transmitted, by plant messenger substances, into noninfected tissue, where, again, they result in defence reactions being triggered, and interfere with the development of secondary infections (systemic acquired resistance, SAR) (Ryals et al., The Plant Cell 8, 1809-1819, 1996).

A series of endogenous plant signal substances which are involved in stress tolerance or pathogen defence are already known. The following may be mentioned: salicylic acid, benzoic acid, jasmonic acid or ethylene (Biochemistry and Molecular Biology of Plants, pp. 850-929, American Society of Plant Physiologists, Rockville, Md., eds. Buchanan, Gruissem, Jones, 2000). Some of these substances or their stable synthetic derivatives and derived structures are also effective when applied externally to plants, or as seed dressing, and activate defence reactions which result in an enhanced stress or pathogen tolerance of the plant (Sembdner, Parthier, Ann. Rev. Plant Physiol. Plant Mol. Biol. 44, 569-589, 1993). The salicylate-mediated defence is directed especially against phytopathogenic fungi, bacteria and viruses (Ryals et al., The Plant Cell 8, 1809-1819, 1996).

A known synthetic product with an action comparable to that of salicylic acid, and which is capable of exerting a protective effect against phytopathogenic fungi, bacteria and viruses, is benzothiadiazole (CGA 245704; common name: Acibenzolar-5-methyl; trade name: Bion®) (Achuo et al., Plant Pathology 53 (1), 65-72, 2004; Tamblyn et al., Pesticide Science 55 (6), 676-677, 1999; EP-OS 0 313 512).

Other compounds which belong to the group of the oxylipins such as, for example, jasmonic acid, and the protective mechanisms which they trigger, are especially active against harmful insects (Walling, J. Plant Growth Regul. 19, 195-216, 2000).

It is furthermore known that the treatment of plants with insecticides from the neonicotinoid (chloronicotinyl) series leads to increased resistance of the plant to abiotic stress. This applies, in particular, to the substance imidacloprid (Brown et al., Beltwide Cotton Conference Proceedings 2231-2237, 2004). This protection is generated by the physiological and biochemical properties of the plant cells being affected, such as, for example, by improving membrane stability, increasing the carbohydrate concentration, enhancing the polyol concentration and antioxidant activity (Gonias et al., Beltwide Cotton Conference Proceedings 2225-2229, 2004).

The effect of chloronicotinyls against biotic stress factors is furthermore known (Crop Protection 19 (5), 349-354, 2000; Journal of Entomological Science 37(1), 101-112, 2002; Annals of Biology (Hisar, India) 19 (2), 179-181, 2003). For example, insecticides from the neonicotinoid (chloronicotinyl) series lead to the enhanced expression of genes from the series of the pathogenesis-related proteins (PR proteins). PR proteins support the plants primarily in the defence against biotic stress factors, such as, for example, phytopathogenic fungi, bacteria and viruses (DE 10 2005 045 174 A; DE 10 2005 022 994 A and WO 2006/122662 A; Thielert Pflanzenschutz-Nachrichten Bayer, 59 (1), 73-86, 2006; Francis et al., European Journal of Plant Pathology, publ. online 23.1.2009).

It is furthermore known that the treatment of genetically modified plants with insecticides from the neonicotinoid (chloronicotinyl) series leads to an improved stress tolerance of the plant (EP 1 731 037 A), for example also to the herbicide glyphosate (WO 2006/015697 A).

Thus, it is known that plants have available a plurality of endogenous reaction mechanisms which may bring about an effective defence against a wide range of harmful organisms (biotic stress) and/or abiotic stress.

Cultivating healthy and uniformly grown seedlings is an essential prerequisite for the large-scale production and the economical management of agricultural, horticultural and silvicultural crop plants.

A large number of cultivation methods for seedlings are established in agriculture, forestry and horticulture. Cultivation media which are used here are, besides steam soil, also specific media, among which media based on white peat, coconut fibres, rockwool such as, for example, Grodan®, pumice, expanded clay such as, for example, Lecaton® or Lecadan®, clay granules such as, for example, Seramis®, foams, such as, for example, Baystrat®, vermiculites, pearlites, artificial soils, such as, for example, Hygromull® or combinations of these media, into which either fungi- and/or insecticide-treated or else untreated seed is sown.

In special crops such as, for example, tobacco, young plants are increasingly grown by what is known as the float method or floating method (Leal, R. S., The use of Confidor S in the float, a new tobacco seedlings production system in the South of Brazil. Pflanzenschutz-Nachrichten Bayer (German edition) (2001), 54(3), pages 337 to 352; Rudolph, R. D.; Rogers, W. D.; The efficacy of imidacloprid treatment for reduction in the severity of insect vectored virus diseases of tobacco. Pflanzenschutz-Nachrichten Bayer (German edition) (2001), 54(3), pages 311 to 336). In this method, the seed is sown into specific containers, for example perforated Styropor trays, in specific, peat-medium-based compost, and subsequently cultured in containers with a suitable nutrient solution until the seedlings have reached the desired transplant size (FIG. 1). Here, the containers are allowed to float on the nutrient solution, which gives the cultivation method its name (Leal, 2001, see above). In floating methods, insecticides from the neonicotinoid (chloronicotinyl) class have been employed for some years for controlling sucking pests. In the float method, the plants are usually sprayed with neonicotinoid (chloronicotinyl) insecticides shortly before transplanting, or drenched with neonicotinoid (chloronicotinyl) insecticides immediately before or during transplanting in the field (Leal, 2001, see above; Rudolph and Rogers, 2001, see above). Both application methods are technically relatively complicated.

Here, fungicides and insecticides are used up to the transplantation in order to protect the emerging generative or vegetative propagation material from fungal pathogens and pests. The choice of the plant protection products, the site and timing of application, and the application rate of the compositions depends in this context mainly on the type of the fungal diseases and pests which are encountered, the specific mode of action and duration of action of the compositions and on the plant tolerance, and can thus be adapted directly to the specific requirements of a variety of crops and regions.

Sulphoximines have been described for example as agents for controlling animal pests, in particular insects (for example US patent application 2005/228027 A1, WO 2006/060029 A2, WO 2007/095229 A2, WO 2007/149134 A1, WO 2008/027539 A1, WO 2008/027073 A1 and WO 2008/097235 A1). Moreover, the enhanced insecticidal activity by means of adding suitable salts and, if appropriate, additives has been described for a subgroup of sulphoximines (WO 2007/068355).

It is not known from the prior art that sulphoximines are active against biotic stress factors and/or abiotic stress of plants, or with regard to plant growth.

It has now been found that sulphoximines are suitable for enhancing the plants' intrinsic defences (pathogen defence in plants).

Here, the sulphoximines result in a good protection of the plants from the damage by fungal, bacterial or viral pathogens, independently of a control of insects. Without wanting to be bound by theory, it is currently assumed that the defence against the pathogens is the result of the induction of PR proteins as a consequence of a treatment with at least one sulphoximine.

The use according to the invention shows the above-described advantages in particular in the treatment of seed, of the soil, in specific cultivation and growing methods (for example floating box, rockwool, hydroponics), but also in the treatment of stems and leaves. Combinations of sulphoximines with, inter alfa, insecticides, fungicides and bactericides show a synergistic effect on the control of plant diseases. The combined use of sulphoximines together with genetically modified varieties with regard to an elevated abiotic stress tolerance additionally leads to a synergistically improved growth.

Finally, it has also been found in accordance with the invention that sulphoximines are suitable not only for enhancing pathogen defence in plants, but also for improving plant growth and/or for enhancing the resistance of plants to plant diseases which are caused by fungi, bacteria, viruses, MLOs (mycoplasma-like organisms) and/or RLOs (rickettsia-like organisms), in particular to soil-borne fungal diseases, and/or for increasing the resistance of plants to abiotic stress factors.

The abiotic stress factors may include, for example, drought, cold and heat conditions, osmotic stress, waterlogging, increased soil salinity, increased exposure to minerals, ozone conditions, strong light conditions, limited availability of nitrogen nutrients, limited availability of phosphorus nutrients or the avoidance of shade.

The present invention therefore firstly relates to the use of at least one compound selected from the class of the sulphoximines for enhancing plants' intrinsic defences and/or for improving plant growth and/or for enhancing the resistance of plants to plant diseases which are caused by fungi, bacteria, viruses, MLOs (mycoplasma-like organisms) and/or RLOs (rickettsia-like organisms), in particular to soil-borne fungal diseases, and/or for enhancing the resistance of plants to abiotic stress factors.

Especially suitable sulphoximines are described by the general formula (I):

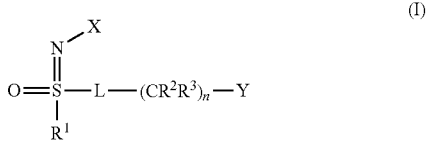

in which

X represents $NO_2$, CN or $COOR^4$,

L represents a single bond, $R^1$ represents $C_1$-$C_4$-alkyl, or $R^1$, sulphur and L together represent a 4-, 5- or 6-membered ring, $R^2$ and $R^3$ independently of one another represent hydrogen, methyl, ethyl, fluorine, chlorine or bromine, or $R^2$ and $R^3$ together represent —$(CH_2)_2$—, —$(CH_2)_3$—, —$(CH_2)_4$— or —$(CH_2)_5$— and, together with the carbon atom to which they are bonded, form a 3-, 4-, 5- or 6-membered ring, n represents 0, 1, 2 or 3, Y represents one of the radicals

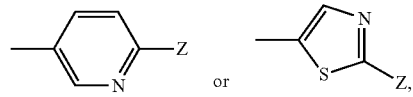

in which

Z represents halogen, $C_1$-$C_4$-alkyl, $C_1$-$C_4$-haloalkyl, $C_1$-$C_4$-alkoxy or $C_1$-$C_4$-haloalkoxy and $R^4$ represents $C_1$-$C_3$-alkyl.

Depending on the nature of the substituents, the compounds of the formula (I) can also be present as optical isomers or isomer mixtures in various compositions, which, if appropriate, can be separated in a customary manner. Not only the pure isomers, but also the isomer mixtures, their use and compositions comprising them are subject-matter of the present invention. For the sake of simplicity, however, the text which follows will always mention compounds of the formula (I) although this is understood as meaning not only the pure compounds but, if appropriate, also mixtures with various proportions of isomeric compounds.

Preferred sub-groups of the compounds of the formula (I) are mentioned in the text which follows:

In an emphasized group (Ia) of compounds of the formula (I), X represents the nitro group:

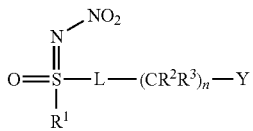

(Ia)

In a further emphasized group (Ib) of compounds of the formula (I), X represents the cyano group:

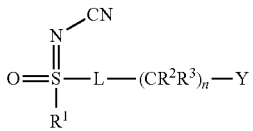

(Ib)

In a further emphasized group (Ic) of compounds of the formula (I), X represents $NO_2$ or CN, Y represents the 6-chloropyrid-3-yl radical:

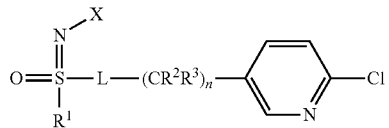

(Ic)

In a further emphasized group (Id) of compounds of the formula (I), X represents $NO_2$ or CN, Y represents the 6-trifluoromethylpyrid-3-yl radical:

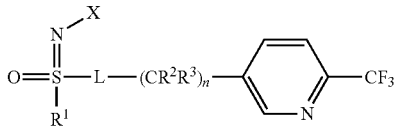

(Id)

In a further emphasized group (Ie) of compounds of the formula (I), X represents $NO_2$ or CN, Y represents the 2-chloro-1,3-thiazol-5-yl radical:

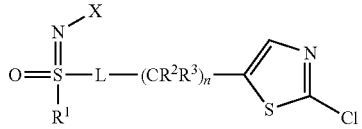

(Ie)

In a further emphasized group (If) of compounds of the formula (I), X represents $NO_2$ or CN, Y represents the 2-trifluoromethyl-1,3-thiazol-5-yl radical:

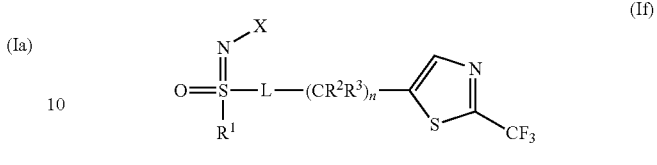

(If)

In a further emphasized group (Ig) of compounds of the formula (I), R', sulphur and L together form a 5-membered ring, X represents $NO_2$ or CN, Y represents 6-halopyrid-3-yl or 6-($C_1$-$C_4$-haloalkyl)pyrid-3-yl, especially preferably 6-chloropyrid-3-yl or 6-trifluoromethylpyrid-3-yl, n preferably represents 0:

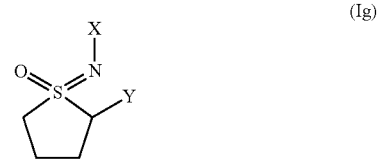

(Ig)

In a further emphasized group (Ih) of compounds of the formula (I), $R^1$, sulphur and L together form a 5-membered ring, X represents $NO_2$ or CN, Y represents 6-halopyrid-3-yl or 6-($C_1$-$C_4$-haloalkyl)pyrid-3-yl, especially preferably 6-chloropyrid-3-yl or 6-trifluoromethylpyrid-3-yl, n preferably represents 0:

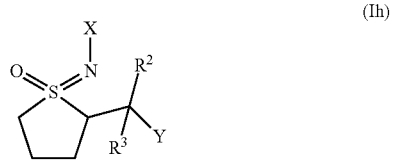

(Ih)

In a further emphasized group (Ii) of compounds of the formula (I), $R^1$ represents methyl, X represents $NO_2$ or CN, L represents a single bond and n preferably represents 1:

(Ii)

In a further emphasized group (Ij) of compounds of the formula (I), $R^1$ represents methyl, $R^2$ and $R^3$ independently of one another represent hydrogen or methyl, X represents $NO_2$ or CN, n preferably represents 1:

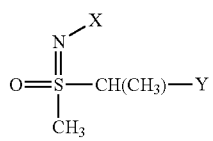

In a further emphasized group (Ik) of compounds of the formula (I), $R^1$ represents methyl, $R^2$ and $R^3$ together form $-(CH_2)_2-$ and together with the carbon atom to which they are bonded form a 3-membered ring, X represents $NO_2$ or CN, n preferably represents 1:

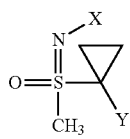

Depending on the nature of the substituents, the compounds of the general formula (I) can, if appropriate, be present as geometric and/or optically active isomers or as corresponding isomer mixtures of various compositions. The invention relates not only to the pure isomers, but also to the isomer mixtures.

The following compounds of the formula (I) may be mentioned individually:

Compound (I-1), N-[6-chloropyridin-3-yl]methyl](methyl)oxido-$\lambda^4$-sulphanylidenecyanamide:

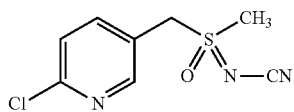

disclosed in US Patent Application 2005/228027 A1 and WO 2007/149134 A1.

Compound (I-2), N-[6-trifluoromethylpyridin-3-yl]methyl](methyl)oxido-$\lambda^4$-sulphanylidenecyanamide:

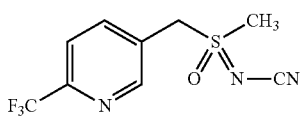 [SMILES: CS(=O)(Cc1ccc(C(F)(F)F)nc1)=NC#N]

disclosed in WO 2007/095229 A2, WO 2007/149134 A1 and WO 2008/027073 A1.

Compound (I-3), N-methyl(oxido){[2-chloro-1,3-thiazol-5-yl]methyl}$\lambda^4$-sulphanylidenecyanamide:

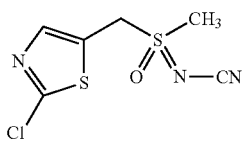

disclosed in US Patent Application 2005/228027 A1.

Compound (I-4), N-methyl(oxido){[2-(trifluoromethyl)-1,3-thiazol-5-yl]methyl}$\lambda^4$-sulphanylidenecyanamide:

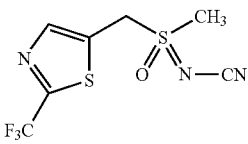 [SMILES: CS(=O)(Cc1cnc(C(F)(F)F)s1)=NC#N]

disclosed in WO 2008/027539 A1.

Compound (I-5), N-[6-chloropyridin-3-yl]ethyl](methyl)oxido-$\lambda^4$-sulphanylidenecyanamide:

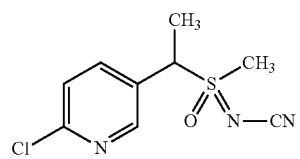

disclosed in US Patent Application 2005/228027 A1 and WO 2007/149134 A1.

Compound (I-6), N-[6-chloropyridin-3-yl]ethyl](methyl)oxido-$\lambda^4$-sulphanylidenecyanamide diastereomer:

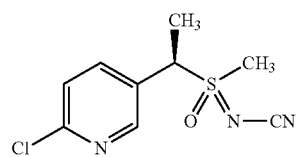

disclosed in US Patent Application 2005/228027 A1 and WO 2007/149134 A1.

Compound (I-7), N-[6-chloropyridin-3-yl]ethyl](methyl)oxido-$\lambda^4$-sulphanylidenecyanamide diastereomer:

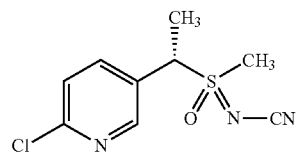

disclosed in US Patent Application 2005/228027 A1 and WO 2007/149134 A1.

Compound (I-8), N-[6-trifluoromethylpyridin-3-yl]ethyl](methyl)oxido-$\lambda^4$-sulphanylidenecyanamide:

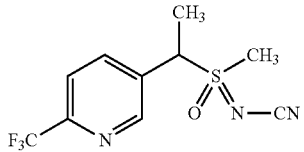

disclosed in WO 2007/095229 A2 and WO 2007/149134 A1.

Compound (I-9), N-[6-(1,1-difluoroethyl)pyrid-3-yl]ethyl](methyl)oxido-λ⁴-sulphanylidenecyanamide:

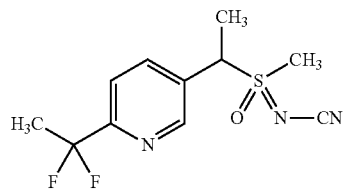 [SMILES: CC(c1ccc(C(C)(F)F)nc1)S(C)(=O)=NC#N]

disclosed in WO 2007/095229 A2.

Compound (I-10), N-[6-difluoromethylpyrid-3-yl]ethyl](methyl)oxido-λ⁴-sulphanylidenecyanamide:

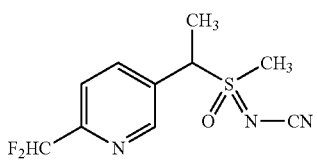 [SMILES: CC(c1ccc(C(F)F)nc1)S(C)(=O)=NC#N]

disclosed in WO 2007/095229 A2.

Compound (I-11), N-methyl(oxido){1-[2-(trichloromethyl)pyrid-3-yl]ethyl}λ⁴-sulphanylidenecyanamide:

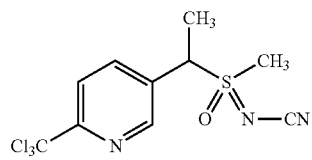

disclosed in WO 2007/095229 A2.

Compound (I-12), N-methyl(oxido){1-[2-(pentafluoroethyl)pyrid-3-yl]ethyl}λ⁴-sulphanylidenecyanamide:

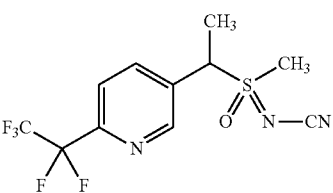 [SMILES: CC(c1ccc(C(F)(F)C(F)(F)F)nc1)S(C)(=O)=NC#N]

disclosed in WO 2007/095229 A2.

Compound (I-13), N-[6-chlorodifluoromethylpyrid-3-yl]ethyl](methyl)oxido-λ⁴-sulphanylidenecyanamide:

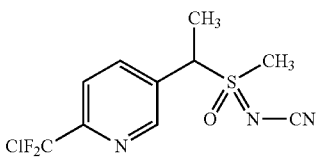

disclosed in WO 2007/095229 A2.

Compound (I-14), N-methyl(oxido){1-[2-(trifluoromethyl)-1,3-thiazol-5-yl]ethyl}λ⁴-sulphanylidenecyanamide:

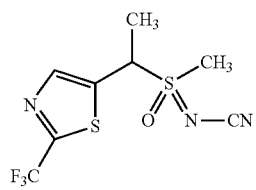 [SMILES: CC(c1cnc(C(F)(F)F)s1)S(C)(=O)=NC#N]

disclosed in WO 2008/027539 A1.

Compound (I-15), N-methyl(oxido){1-[6-(trifluoromethyl)pyridin-3-yl]cyclopropyl-λ⁴-sulphanylidenecyanamide:

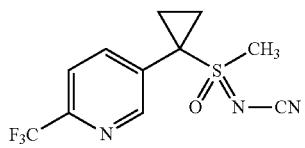 [SMILES: CS(=O)(=NC#N)C1(c2ccc(C(F)(F)F)nc2)CC1]

disclosed in WO 2008/027073 A1.

Compound (I-16), N-methyl(oxido){1-(6-chloropyridin-3-yl)cyclopropyl-λ⁴-sulphanylidenecyanamide:

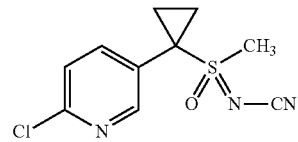 [SMILES: CS(=O)(=NC#N)C1(c2ccc(Cl)nc2)CC1]

disclosed in WO 2008/027073 A1.

Compound (I-17), N-2-(6-chloropyridin-3-yl)-1-oxidotetrahydro-1H-1λ⁴-thienylidenecyanamide:

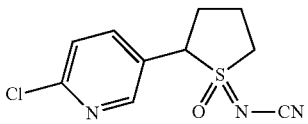 [SMILES: N#CN=S1(=O)CCCC1c1ccc(Cl)nc1]

disclosed in WO 2004/149134 A1.

Compound (I-18), N-2-(6-trifluoromethylpyridin-3-yl)-1-oxidotetrahydro-1H-1λ⁴-thienylidenecyanamide:

disclosed in WO 2004/149134 A1.

Compound (I-19), N-1-oxo-2-(2-trifluoromethyl-1,3-thiazol-5-ylmethyl)tetrahydro-1-$\lambda^6$-thiophen-1-ylidenecyanamide:

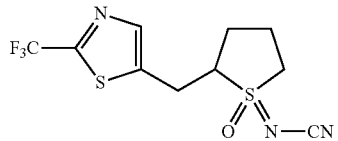 [SMILES: N#CN=S1(=O)CCCC1Cc1cnc(C(F)(F)F)s1]

disclosed in WO 2008/027539 A1.

Compound (I-20), N-1-oxo-2-(6-trifluoromethylpyrid-3-ylmethyl)tetrahydro-1-$\lambda^6$-thiophen-1-ylidenecyanamide:

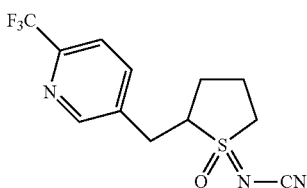 [SMILES: N#CN=S1(=O)CCCC1Cc1ccc(C(F)(F)F)nc1]

disclosed in WO 2007/095229 A2.

Compound (I-21), N-1-oxo-2-(6-chloropyrid-3-ylmethyl)tetrahydro-1-$\lambda^6$-thiophen-1-ylidenecyanamide:

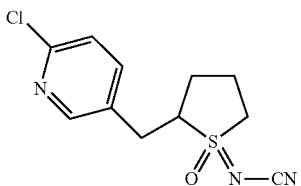 [SMILES: N#CN=S1(=O)CCCC1Cc1ccc(Cl)nc1]

disclosed in US Patent Application 2005/228027 A1.

Compound (I-22), N-1-oxo-2-(6-chloropyrid-3-ylmethyl)tetrahydro-1-$\lambda^6$-thiophen-1-ylidenecyanamide diastereomer:

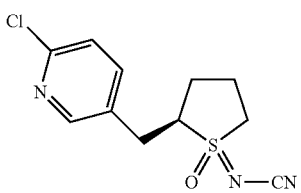 [SMILES: N#CN=S1(=O)CCC[C@@H]1Cc1ccc(Cl)nc1]

disclosed in US Patent Application 2005/228027 A1.

Compound (I-23), N-1-oxo-2-(6-chloropyrid-3-ylmethyl)tetrahydro-1-$\lambda^6$-thiophen-1-ylidenecyanamide diastereomer:

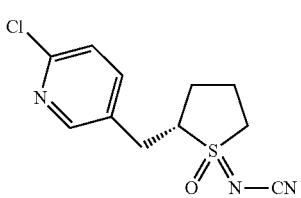 [SMILES: N#CN=S1(=O)CCC[C@H]1Cc1ccc(Cl)nc1]

disclosed in US Patent Application 2005/228027 A1.

The following sulphoximines of the formula (I) are preferred:

(I-1), N-[6-chloropyridin-3-yl]methyl](methyl)oxido-$\lambda^4$-sulphanylidenecyanamide, (I-2), N-[6-trifluoromethylpyridin-3-yl]methyl](methyl)oxido-$\lambda^4$-sulphanylidenecyanamide, (I-3), N-methyl(oxido){[2-chloro-1,3-thiazol-5-yl]methyl}-$\lambda^4$-sulphanylidenecyanamide, (I-4), N-methyl(oxido){[2-(trifluoromethyl)-1,3-thiazol-5-yl]methyl}-$\lambda^4$-sulphanylidenecyanamide, (I-5), N-[6-chloropyridin-3-yl]ethyl](methyl)oxido-$\lambda^4$-sulphanylidenecyanamide, (I-6), N-[6-chloropyridin-3-yl]ethyl](methyl)oxido-$\lambda^4$-sulphanylidenecyanamide diastereomer, (I-7), N-[6-chloropyridin-3-yl]ethyl](methyl)oxido-$\lambda^4$-sulphanylidenecyanamide diastereomer, (I-8), N-[6-trifluoromethylpyridin-3-yl]ethyl](methyl)oxido-$\lambda^4$-sulphanylidenecyanamide, (I-14), N-methyl(oxido){1-[2-(trifluoromethyl)-1,3-thiazol-5-yl]ethyl}-$\lambda^4$-sulphanylidenecyanamide, (I-15), N-methyl(oxido){1-[6-(trifluoromethyl)pyridin-3-yl]cyclopropyl-$\lambda^4$-sulphanylidenecyanamide, (I-16), N-methyl(oxido){1-(6-chloropyridin-3-yl)cyclopropyl-$\lambda^4$-sulphanyldenecyanamide Especially preferred are the following sulphoximines of the formula (I):

(I-5), N-[6-chloropyridin-3-yl]ethyl](methyl)oxido-$\lambda^4$-sulphanylidenecyanamide, (I-6), N-[6-chloropyridin-3-yl]ethyl](methyl)oxido-$\lambda^4$-sulphanylidenecyanamide diastereomer, (I-7), N-[6-chloropyridin-3-yl]ethyl](methyl)oxido-$\lambda^4$-sulphanylidenecyanamide diastereomer, (I-8), N-[6-trifluoromethylpyridin-3-yl]ethyl](methyl)oxido-$\lambda^4$-sulphanylidenecyanamide, (I-15), N-methyl(oxido) {1-[6-(trifluoromethyl)pyridin-3-yl]cyclopropyl-$\lambda^4$-sulphanylidenecyanamide, (I-16), N-methyl(oxido){1-(6-chloropyridin-3-yl)cyclopropyl-$\lambda^4$-sulphanylidenecyanamide.

When, within the scope of the present invention, the text mentions sulphoximines, these are generally sulphoximines of the general formula (I), it being possible in particular for the compounds of the groups (Ia) to (Ik), specifically for the compounds of the general formulae (I-1) to (I-23) to come to be embraced by the general formula (I).

In accordance with the invention, it has been demonstrated that the sulphoximines have an activity according to the invention on the growth of plants.

The term "growth of plants" is understood as meaning within the scope of the present invention various advantages for plants which are not directly connected to the known pesticidal activity, preferably the insecticidal activity, of the sulphoximines, in particular of the sulphoximines of the general formula (I). Such advantageous properties are, for example, the improved plant characteristics mentioned hereinbelow: accelerated germination and emergence of the generative and vegetative propagation material, improved root growth regarding surface area and depth, enhanced development of stolons or tillers, stronger and more productive stolons and tillers, improved shoot growth, increased standing power, increased shoot base diameters, increased leaf area, higher yields of nutrients and constituents such as, for example, carbohydrates, fats, oils, proteins, vitamins, minerals, essential oils, dyes, fibres, better fibre quality, earlier flowering, increased number of flowers, reduced content of toxic products such as mycotoxins, reduced content of residues or any type of disadvantageous components or better digestability, better storability of the harvested crop, improved tolerance to disadvantageous temperatures, improved tolerance to drought and dryness and also lack of oxygen as the result of water logging, improved tolerance to elevated soil salinity and water, increased tolerance to UV radiation, increased tolerance to ozone stress, improved tolerance to herbicides and other plant treatment agents, improved water uptake and photosynthetic rate, advantageous plant properties such as, for example, accelerated maturation, more uniform maturation, greater attraction for beneficial animals, improved pollination, or other advantages which are well known to a person skilled in the art.

As is known, the various advantages for plants, which have been mentioned further above, can be combined in parts, and generally applicable terms can be used to describe them. Such terms are, for example, the following: phytotonic effect, resistance to stress factors, less plant stress, plant health, healthy plants, plant fitness, plant wellness, plant concept, vigor effect, stress shield, protective shield, crop health, crop health properties, crop health products, crop health management, crop health therapy, plant health, plant health properties, plant health products, plant health management, plant health therapy, greening effect or regreening effect, freshness, or other terms with which a person skilled in the art is quite familiar.

It has been demonstrated that the sulphoximines of the general formula (I) have a good effect on the growth of plants. Within the scope of the present invention, the term "good effect" is understood as meaning, but not by limitation, at least an emergence which is improved by in general 5%, in particular 10%, especially preferably 15%, specifically 20%, at least an increased yield which is in general 5%, in particular 10%, especially preferably 15%, specifically 20%, at least an improved root development which is in general 5%, in particular 10%, especially preferably 15%, specifically 20%, at least an increased shoot length which is in general 5%, in particular 10%, especially preferably 15%, specifically 20%, at least an increased leaf area which is in general 5%, in particular 10%, especially preferably 15%, specifically 20%, at least an improved germination which is in general 5%, in particular 10%, especially preferably 15%, specifically 20%, at least an improved photosynthetic rate which is in general 5%, in particular 10%, especially preferably 15%, specifically 20%, it being possible for the effects to manifest themselves individually or else in any combination of two or more effects.

In accordance with the invention, it has additionally been found that the application, to plants or to their environment, of sulphoximines in combination with a fertilizer as defined hereinbelow brings about a synergistic growth-promoting effect.

Fertilizers which can be employed in accordance with the invention together with the sulphoximines which have been explained in greater detail hereinabove are generally organic and inorganic nitrogen-containing compounds such as, for example, ureas, urea/formaldehyde condensates, amino acids, ammonium salts and ammonium nitrates, potassium salts (preferably chlorides, sulphates, nitrates), salts of phosphoric acid and/or salts of phosphorous acid (preferably potassium salts and ammonium salts). Those which must be mentioned in particular in this context are the NPK fertilizers, i.e. fertilizers which contain nitrogen, phosphorus and potassium, calcium ammonium nitrate, i.e. fertilizers which additionally contain calcium, or ammonia nitrate sulphate (general formula $(NH_4)_2SO_4\ NH_4NO_3$), ammonium phosphate and ammonium sulphate. These fertilizers are generally known to the skilled worker, see also, for example, Ullmann's Encyclopedia of Industrial Chemistry, 5th Edition, Vol. A 10, pages 323 to 431, Verlagsgesellschaft, Weinheim, 1987.

The fertilizers may also contain salts of micronutrients (preferably calcium, sulphur, boron, manganese, magnesium, iron, boron, copper, zinc, molybdenum and cobalt) and phytohormones (for example vitamin B1 and indole-3-acetic acid (IAA)) or mixtures of these. Fertilizers employed in accordance with the invention may also contain other salts such as monoammonium phosphate (MAP), diammonium phosphate (DAP), potassium sulphate, potassium chloride or magnesium sulphate. Suitable amounts of the secondary nutrients, or trace elements, are amounts of from 0.5 to 5% by weight, based on the totality of the fertilizer. Other possible constituents are plant protectants, insecticides or fungicides, growth regulators or mixtures of these. This will be explained in detail further below.

The fertilizers can be employed for example in the form of powders, granules, prills or compactates. However, the fertilizers can also be employed in liquid form, dissolved in an aqueous medium. In this case, dilute aqueous ammonia may also be employed as nitrogen fertilizer. Further possible constituents of fertilizers are described for example in Ullmann's Encyclopedia of Industrial Chemistry, 5th edition, 1987, Vol. A 10, pages 363 to 401, DE-A 41 28 828, DE-A 19 05 834 and DE-A 196 31 764.

The general composition of the fertilizers which, within the scope of the present invention, may take the form of straight and/or compound fertilizers, for example composed of nitrogen, potassium or phosphorus, may vary within a wide range. In general, a content of from 1 to 30% by weight of nitrogen (preferably 5 to 20% by weight), from 1 to 20% by weight of potassium (preferably from 3 to 15% by weight) and a content of from 1 to 20% by weight of phosphorus (preferably from 3 to 10% by weight) is advantageous. The microelement content is usually in the ppm order of magnitude, preferably in the order of magnitude from 1 to 1000 ppm.

Within the scope of the present invention, the fertilizer and the sulphoximine, in particular the sulphoximine of the general formula (I), may be applied simultaneously, i.e. synchronously. However, it is also possible first to employ the fertilizer and then the sulphoximine, or first the sulphoximine and then the fertilizer. In the case of nonsynchronous application of the sulphoximine and the fertilizer, the application within the scope of the present invention is, however, carried out in a functional context, in particular within a period of from in general 24 hours, preferably 18 hours, especially preferably 12 hours, specifically 6 hours, more specifically 4 hours, even more specifically within 2 hours. In very special embodiments of the present invention, the application of the active substances according to the invention of the general formula (I) and of the fertilizer is carried out within a time frame of less than 1 hour, preferably less than 30 minutes, especially preferably less than 15 minutes.

Starting from at least one active substance to be used in accordance with the invention and at least one fertilizer, it is additionally possible to prepare dimensionally stable mixtures, for example in the form of rods, granules, tablets and the like. In order to prepare a suitable dimensionally stable mixture, the components in question can be mixed with one another and, if appropriate, extruded, or the fertilizer can be coated with the at least one active substance of the general formula (I) to be used in accordance with the invention. If appropriate, it is also possible to use formulation auxiliaries in the dimensionally stable mixtures, such as, for example, extenders or adhesives, in order to achieve a dimensional stability of the resulting mixture. As a result of the appropriate dimensional stability, such mixtures are suitable in particular for application in the home and garden sector, i.e. by a private user or hobby gardener, which can use the dimensionally stable mixture, or the components which are present therein, in a predetermined, precisely defined amount and without particular auxiliaries.

Independently of the above, the mixtures of at least one of the active substances to be used in accordance with the invention and the at least one fertilizer may also be present in liquid form, so that the resulting mixture can be applied as what is known as a tank mix, for example by a professional user in the agricultural sector.

Using at least one of the active substances to be used in accordance with the invention and at least one fertilizer makes it possible to increase root growth, which, in turn, makes possible a higher nutrient uptake, thereby promoting plant growth.

The active substances to be used in accordance with the invention, if appropriate in combination with fertilizers, can preferably be employed in the following plants, the enumeration which follows not being limiting.

Preferred plants are those from the group of the useful plants, ornamentals, turfs, generally used trees which are employed as ornamentals in the public and domestic sectors, and forestry trees. Forestry trees comprise trees for the production of timber, cellulose, paper and products made from parts of the trees.

The term useful plants as used in the present context refers to crop plants which are employed as plants for obtaining foodstuffs, feedstuffs, fuels or for industrial purposes.

The useful plants which can be improved with the method according to the invention include for example the following types of plants: turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao beans and peanuts; cucurbits, for example pumpkin/squash, cucumbers and melons; fibre plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; Lauraceae, for example avocado, Cinnamomum, camphor, or also plants such as tobacco, nuts, coffee, aubergine, sugarcane, tea, pepper, grapevines, hops, bananas, latex plants and ornamentals, for example flowers, shrubs, deciduous trees and coniferous trees. This enumeration is no limitation.

The following plants are considered to be particularly suitable target crops for applying the method according to the invention: cotton, aubergine, turf, pome fruit, stone fruit, soft fruit, maize, wheat, barley, cucumber, tobacco, vines, rice, cereals, pear, beans, soybeans, oilseed rape, tomato, bell pepper, melons, cabbage, potatoes and apples.

Examples of trees which can be improved in accordance with the method according to the invention are: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved in accordance with the method according to the invention are: from the tree species *Aesculus*: *A. hippocastanum, A. pariflora, A. carnea*; from the tree species *Platanus*: *P. aceriflora, P. occidentalis, P. racemosa*; from the tree species *Picea*: *P. abies*; from the tree species *Pinus*: *P. radiate, P. ponderosa, P. contorta, P. sylvestre, P. elliottii, P. montecola, P. albicaulis, P. resinosa, P. palustris, P. taeda, P. flexilis, P. jeffregi, P. baksiana, P. strobes*; from the tree species *Eucalyptus*: *E. grandis, E. globulus, E. camadentis, E. nitens, E. obliqua, E. regnans, E. pilularus*.

Especially preferred trees which can be improved in accordance with the method according to the invention are: from the tree species *Pinus*: *P. radiate, P. ponderosa, P. contorta, P. sylvestre, P. strobes*; from the tree species *Eucalyptus*: *E. grandis, E. globulus, E. camadentis*.

Very particularly preferred trees which can be improved in accordance with the method according to the invention are: horsechestnut, Platanaceae, linden tree, maple tree.

The present invention can also be applied to any turf grasses, including cool-season turf grasses and warm-season turf grasses. Examples of cold-season turf grasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.);

fescues (*Festuca* spp.), such as red fescue (*Festuca rubra* L. spp. rubra), creeping fescue (*Festuca rubra* L.), chewings fescue (*Festuca rubra* commutata Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turfgrasses are beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog's-tail (*Cynosurus cristatus* L.).

Examples of warm-season turfgrasses are Bei nudagrass (*Cynodon* spp. L. C. Rich), zoysiagrass (*Zoysia* spp. Willd.), St. Augustine grass (*Stenotaphrum secundatum* Walt Kuntze), centipedegrass (*Eremochloa ophiuroides* Munro Hack.), carpetgrass (*Axonopus affinis* Chase), Bahia grass (*Paspalum notatum* Flugge), Kikuyugrass (*Pennisetum clandestinum* Hochst. ex Chiov.), buffalo grass (*Buchloe dactyloids* (Nutt.) Engelm.), Blue gramma (*Bouteloua gracilis* (H.B.K.) Lag. ex Griffiths), seashore paspalum (*Paspalum vaginatum* Swartz) and sideoats grama (*Bouteloua curtipendula* (Michx. Torr.). Cool-season turfgrasses are generally preferred for the use according to the invention. Especially preferred are bluegrass, benchgrass and redtop, fescues and ryegrasses. Bentgrass is especially preferred.

It has furthermore been found that sulphoximines of the general formula (I) leads to an increased expression of genes from the series of the pathogenesis-related proteins (PR proteins). PR proteins support the plants primarily in the defence against biotic stress factors such as, for example, phytopathogenic fungi, bacteria and viruses. As a consequence, plants are better protected from infection with phytopathogenic fungi, bacteria and viruses after the application of sulphoximines, in particular of sulphoximines of the general formula (I). Upon the necessary use of insecticides, fungicides and bactericides in a mixture and also in the sequential application together with sulphoximines, in particular with sulphoximines of the general formula (I), the activity of the former is supported.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkyl aryl and/or POP-POE ethers, fat- and/or POP-POE adducts, POE and/or POP polyol derivatives, POE and/or POP sorbitan- or sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

The invention furthermore relates to the use of sulphoximines, in particular of sulphoximines of the general formula (I), for protecting plants against plant diseases which are caused by fungi, bacteria, viruses, MLOs (Mycoplasma-like organisms) and/or RLOs (Rickettsia-like organisms). Independently of an insect control, the sulphoximines lead to a good protection of the plant from damage by fungal, bacterial or viral pathogens.

Advantages over other methods which are possible are the low application rates required for achieving this protection, and the good plant tolerance of the sulphoximines of the general formula (I). Moreover, a protection against a multiplicity of pathogens can be achieved with only one active substance.

To obtain protection from pathogens, in particular against plant diseases which are caused by fungi, bacteria, viruses, MLOs (Mycoplasma-like organisms) and/or RLOs (Rickettsia-like organisms), the plants can be treated with individual active substances or with combinations of sulphoximines of the general formula (I).

Furthermore, the positive activity which has been described of the sulphoximines on the plants' intrinsic defences can be supported by an additional treatment with insecticidal, fungicidal or bactericidal active substances.

In a preferred embodiment, this protection is effected by inducing PR proteins as the result of the treatment with sulphoximines of the general formula (I).

Preferred sulphoximines of the general formula (I) are:
(I-1), N-[6-chloropyridin-3-yl]methyl](methyl)oxido-$\lambda^4$-sulphanylidenecyanamide
(I-2), N-[6-trifluoromethylpyridin-3-yl]methyl](methyl)oxido-$\lambda^4$-sulphanylidenecyanamide
(I-3), N-methyl(oxido){[2-chloro-1,3-thiazol-5-yl]methyl}-$\lambda^4$-sulphanylideneeyanamide
(I-4), N-methyl(oxido){[2-(trifluoromethyl)-1,3-thiazol-5-yl]methyl}-$\lambda^4$-sulphanylidenecyanamide
(I-5), N-[6-chloropyridin-3-yl]ethyl](methyl)oxido-$\lambda^4$-sulphanylidenecyanamide
(I-6), N-[6-chloropyridin-3-yl]ethyl](methyl)oxido-$\lambda^4$-sulphanylidenecyanamide diastereomer
(I-7), N-[6-chloropyridin-3-yl]ethyl](methyl)oxido-$\lambda^4$-sulphanylidenecyanamide diastereomer
(I-8), N-[6-trifluoromethylpyridin-3-yl]ethyl](methyl)oxido-$\lambda^4$-sulphanylidenecyanamide
(I-9), N-[6-(1,1-difluoroethyl)pyrid-3-yl]ethyl](methyl)oxido-$\lambda^4$-sulphanylidenecyanamide
(I-10), N-[6-difluoromethylpyrid-3-yl]ethyl](methyl)oxido-$\lambda^4$-sulphanylidenecyanamide
(I-11), N-methyl(oxido) {1-[2-(trichloromethyl)pyrid-3-yl]ethyl}-$\lambda^4$-sulphanylidenecyanamide
(I-12), N-methyl(oxido) {1-[2-(pentafluoroethyl)pyrid-3-yl]ethyl}-$\lambda^4$-sulphanylidenecyanamide
(I-13), N-[6-chlorodifluoromethylpyrid-3-yl]ethyl](methyl)oxido-$\lambda^4$-sulphanylidenecyanamide
(I-14), N-methyl(oxido) {1-[2-(trifluoromethyl)-1,3-thiazol-5-yl]ethyl}-$\lambda^4$-sulphanylidenecyanamide
(I-15), N-methyl(oxido) {1-[6-(trifluoromethyl)pyridin-3-yl]cyclopropyl-$\lambda^4$-sulphanylidenecyanamide
(I-16), N-methyl(oxido) {1-(6-chloropyridin-3-yl)cyclopropyl-$\lambda^4$-sulphanylidenecyanamide
(I-17), N-2-(6-chloropyridin-3-yl)-1-oxidotetrahydro-1H-1$\lambda^4$-thienylidenecyanamide
(I-18), N-2-(6-trifluoromethylpyridin-3-yl)-1-oxidotetrahydro-1H-1$\lambda^4$-thienylidenecyanamide
(I-19), N-1-oxo-2-(2-trifluoromethyl-1,3-thiazol-5-ylmethyl)tetrahydro-1-$\lambda^6$-thiophen-1-ylidenecyanamide
(I-20), N-1-oxo-2-(6-trifluoromethylpyrid-3-ylmethyl)tetrahydro-1-$\lambda^6$-thiophen-1-ylidenecyanamide
(I-21), N-1-oxo-2-(6-chloropyrid-3-ylmethyl)tetrahydro-1-$\lambda^6$-thiophen-1-ylidenecyanamide
(I-22), N-1-oxo-2-(6-chloropyrid-3-ylmethyl)tetrahydro-1-$\lambda^6$-thiophen-1-ylidenecyanamide diastereomer
(I-23), N-1-oxo-2-(6-chloropyrid-3-ylmethyl)tetrahydro-1-$\lambda^6$-thiophen-1-ylidenecyanamide diastereomer Especially preferred sulphoximines of the general formula (I) are:
(I-1), N-[6-chloropyridin-3-yl]methyl](methyl)oxido-$\lambda^4$-sulphanylidenecyanamide,
(I-2), N-[6-trifluoromethylpyridin-3-yl]methyl](methyl)oxido-$\lambda^4$-sulphanylidenecyanamide,
(I-3), N-methyl(oxido){[2-chloro-1,3-thiazol-5-yl]methyl}-$\lambda^4$-sulphanylidenecyanamide,
(I-4), N-methyl(oxido){[2-(trifluoromethyl)-1,3-thiazol-5-yl]methyl}-$\lambda^4$-sulphanylidenecyanamide,
(I-5), N-[6-chloropyridin-3-yl]ethyl](methyl)oxido-$\lambda^4$-sulphanylidenecyanamide,
(I-6), N-[6-chloropyridin-3-yl]ethyl](methyl)oxido-$\lambda^4$-sulphanylidenecyanamide diastereomer,
(I-7), N-[6-chloropyridin-3-yl]ethyl](methyl)oxido-$\lambda^4$-sulphanylidenecyanamide diastereomer,
(I-8), N-[6-trifluoromethylpyridin-3-yl]ethyl](methyl)oxido-$\lambda^4$-sulphanylidenecyanamide,
(I-14), N-methyl(oxido){1-[2-(trifluoromethyl)-1,3-thiazol-5-yl]ethyl}-$\lambda^4$-sulphanylidenecyanamide,
(I-15), N-methyl(oxido){1-[6-(trifluoromethyl)pyridin-3-yl]cyclopropyl-$\lambda^4$-sulphanylidenecyanamide,
(I-16), N-methyl(oxido) {1-(6-chloropyridin-3-yl)cyclopropyl-$\lambda^4$-sulphanylidenecyanamide.

Very especially preferred sulphoximines of the formula (I) are:
(I-5), N-[6-chloropyridin-3-yl]ethyl](methyl)oxido-$\lambda^4$-sulphanylidenecyanamide,
(I-6), N-[6-chloropyridin-3-yl]ethyl](methyl)oxido-$\lambda^4$-sulphanylidenecyanamide diastereomer,
(I-7), N-[6-chloropyridin-3-yl]ethyl](methyl)oxido-$\lambda^4$-sulphanylidenecyanamide diastereomer,
(I-8), N-[6-trifluoromethylpyridin-3-yl]ethyl](methyl)oxido-$\lambda^4$-sulphanylidenecyanamide,
(I-15), N-methyl(oxido){1-[6-(trifluoromethyl)pyridin-3-yl]cyclopropyl-$\lambda^4$-sulphanylidenecyanamide,
(I-16), N-methyl(oxido){1-(6-chloropyridin-3-yl)cyclopropyl-$\lambda^4$-sulphanylidenecyanamide.

It is especially preferred to treat, in accordance with the invention, plants of the respective plant varieties which are commercially available or in use. Plant varieties are understood as meaning plants with novel properties ("traits") which have been obtained by conventional breeding, by mutagenesis or else with the aid of recombinant DNA techniques. Accordingly, crop plants can be plants which can be obtained by conventional breeding and optimization methods or by biotechnological and recombinant methods or combinations of these methods, including the transgenic plants and including the plant varieties capable or not of being protected by Plant Breeders' Rights.

Thus, the treatment method according to the invention can also be used for the treatment of genetically modified organisms (GMOs), for example plants or seeds. Genetically modified plants (or transgenic plants) are plants in which a heterologous gene has been stably integrated into the genome. The term "heterologous gene" means essentially a gene which is provided or assembled outside the plant and which, upon introduction into the nuclear genome, the chloroplast genome or the mitochondrial genome, imparts to the transformed plant novel or improved agronomical or other traits, because it expresses a protein or polypeptide of interest or because another gene which is present in the plant, or other genes which are present in the plant, are down-regulated or switched off (for example by means of antisense technology, cosuppression technology or RNAi technology [RNA interference]). A heterologous gene which is present in the genome is also referred to as a transgene. A transgene, which is defined by its specific presence in the plant genome, is referred to as transformation event, or transgenic event.

Plants and plant varieties which are preferably to be treated according to the invention include all plants which have genetic material which imparts particularly advantageous, useful traits to these plants (whether obtained by breeding and/or biotechnological means).

Plants and plant varieties which are also preferably to be treated according to the invention are resistant against one or more biotic stress factors, i.e. said plants show a better defence against animal and microbial pests, such as against nematodes, insects, mites, phytopathogenic fungi, bacteria, viruses and/or viroids.

Plants and plant varieties which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased mineral exposure, ozone exposure, high light exposure, limited availability of nitrogen nutrients, limited availability of phosphorus nutrients, shade avoidance.

Plants and plant varieties which may also be treated according to the invention are those plants characterized by enhanced yield characteristics. Increased yield in said plants can be the result of for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including, but not limited to, early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and oil composition, nutritional value, reduction in anti-nutritional compounds, improved processability and better storage stability.

Plants that may be treated according to the invention are hybrid plants that already express the characteristic of heterosis, or hybrid effect, which results in generally higher yield, greater vigour, better health, and resistance towards biotic and abiotic stress factors. Such plants are typically made by crossing an inbred male-sterile parent line (the female parent) with another inbred malefertile parent line (the male parent). Hybrid seed is typically harvested from the male sterile plants and sold to growers. Male sterile plants can sometimes (e.g. in maize) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants it is typically useful to ensure that male fertility is fully restored in the hybrid plants which contain the determinants genetically responsible for male sterility. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Malesterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar (e.g. WO 1991/002069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacteria *Salmonella typhimurium* (Comai et al., Science (1983), 221, 370-371), the CP4 gene of the bacteria *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an eleusine EPSPS (WO 2001/66704). It can also be a mutated EPSPS as described in for example EP-A 0837944, WO 2000/066746, WO 2000/066747 or WO 2002/026995. Glyphosate-tolerant plants can also be obtained by expressing a gene that encodes a glyphosate oxidoreductase enzyme as described in U.S. Pat. Nos. 5,776,760 and 5,463, 175. Glyphosate-tolerant plants can also be obtained by expressing a gene that encodes a glyphosate acetyl transferase enzyme as described in for example WO 2002/036782, WO 2003/092360, WO 2005/012515 and WO 2007/024782. Glyphosate-tolerant plants can also be obtained by selecting plants containing naturally-occurring mutations of the above-mentioned genes, as described in for example WO 2001/024615 or WO 2003/013226.

Other herbicide resistant plants are for example plants that are made tolerant to herbicides inhibiting the enzyme glutamine synthase, such as bialaphos, phosphinotricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinotricin acetyltransferase (such as the bar or pat protein from *Streptomyces* species). Plants expressing an exogenous phosphinotricin acetyltransferase are for example described in U.S. Pat. Nos. 5,561,236; 5,648,477; 5,646,024; 5,273,894; 5,637, 489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (IIPPD). Hydroxyphenylpyruvatedioxygenases are enzymes that catalyse the reaction in which para-hydroxyphenylpyruvate (HPP) is transformed into homogentisate. Plants tolerant to HPPD inhibitors can be transformed with a gene encoding a naturally-occurring resistant HPPD enzyme, or a gene encoding a mutated HPPD enzyme as described in WO 1996/038567, WO 1999/024585 and WO 1999/024586. Tolerance for HPPDinhibitors can also be obtained by transforming plants with genes encoding certain enzymes enabling the formation of homogentisate despite the inhibition of the native HPPD enzymes by the HPPD inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Still further herbicide resistant plants are plants that are made tolerant to acetolactate synthase (ALS) inhibitors. Known ALS inhibitors include, for example, sulphonylurea, imidazolinone, triazolopyrimidines, pyrimidinyloxy(thio)benzoates and/or sulphonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also, in U.S. Pat. Nos. 5,605,011, 5,378,824, 5,141,870 and 5,013,659. The production of sulphonylureatolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and in international publication WO 1996/033270. Other imidazolinone-tolerant plants are also described in for example WO 2004/040012, WO 2004/106529, WO 2005/020673, WO 2005/093093, WO 2006/007373, WO 2006/015376, WO 2006/024351 and WO 2006/060634. Further sulphonylurea- and imidazolinone-tolerant plants are also described in for example WO 2007/024782.

Other plants tolerant to imidazolinone and/or sulphonylurea can be obtained by induced mutagenesis, selection in cell cultures in the presence of the herbicide or mutation breeding as described for example for soybeans in U.S. Pat. No. 5,084,082, for rice in WO 1997/41218, for sugar beet in U.S. Pat. No. 5,773,702 and WO 1999/057965, for lettuce in U.S. Pat. No. 5,198,599 or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:
1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Ae or Cry3Bb or insecticidal portions thereof; or
2) a crystal protein from *Bacillus thuringiensis* or a portion thereof which is insecticidal in the presence of a second crystal protein other than *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or
3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or
5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/Home/Neil_Crickmore/Bt/vip.html, e.g. proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment an insect-resistant plant contains more than one transgene encoding a protein of any one of the above classes 1 to 8, to expand the range of target insect species affected, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stress factors. Such plants can be obtained by genetic transformation or by selection of plants containing a mutation imparting such stress resistance. Particularly useful stress tolerance plants include:
a. plants which contain a transgene capable of reducing the expression and/or the activity of the poly(ADP-ribose) polymerase (PARP) gene in the plant cells or plants as described in WO 2000/004173 or EP 04077984.5 or EP 06009836.5.
b. plants which contain a stress tolerance enhancing transgene capable of reducing the expression and/or the activity of the PARG encoding genes of the plants or plant cells, as described e.g. in WO 2004/090140.
c. plants which contain a stress tolerance enhancing transgene coding for a plant-functional enzyme of the nicotinamide adenine dinucleotide salvage biosynthetic pathway including nicotinamidase, nicotinate phosphoribosyltransferase, nicotinic acid mononucleotide adenyl transferase, nicotinamide adenine dinucleotide synthetase or nicotinamide phosphoribosyltransferase as described e.g. in EP 04077624.7 or WO 2006/133827 or PCT/EP07/002,433.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this modified starch is better suited for special applications. Said transgenic plants synthesizing a modified starch are disclosed, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO 99/58688, WO 1999/58690, WO 1999/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. Nos. 5,824,790, 6,013,861, WO 1994/004693, WO 1994/009144, WO 1994/11520, WO 1995/35026 or WO 1997/20936.

2) transgenic plants which synthesize non-starch carbohydrate polymers or which synthesize non-starch carbohydrate polymers with altered properties in comparison to wild type plants without genetic modification. Examples are plants producing polyfructose, especially of the inulin and levan type, as disclosed in EP 0663956, WO 1996/001904, WO 1996/021023, WO 1998/039460 and WO 1999/024593, plants producing alpha-1,4 glucans as disclosed in WO 1995/031553, US 2002/031826, U.S. Pat. Nos. 6,284,479, 5,712,107, WO 1997/047806, WO 1997/047807, WO 1997/047808 and WO 2000/14249, plants producing alpha-1,6 branched alpha-1,4 glucans, as disclosed in WO 2000/73422, and plants producing alternan, as disclosed in WO 2000/047727, EP 06077301.7, U.S. Pat. No. 5,908,975 and EP 0728213.

3) transgenic plants which produce hyaluronan, as for example disclosed in WO 2006/032538, WO 2007/039314, WO 2007/039315, WO 2007/039316, JP 2006/304779 and WO 2005/012529.

Plants or plant cultivars (that can be obtained by plant biotechnology methods such as genetic engineering) which may also be treated according to the invention are plants, such as cotton plants, with altered fibre characteristics. Such plants can be obtained by genetic transformation or by selection of plants containing a mutation imparting such altered fibre characteristics and include:

a) plants, such as cotton plants, which contain an altered form of cellulose synthase genes as described in WO 1998/000549;

b) plants, such as cotton plants, which contain an altered form of rsw2 or rsw3 homologous nucleic acids as described in WO 2004/053219;

c) plants, such as cotton plants, with increased expression of sucrose phosphate synthase as described in WO 2001/017333;

d) plants, such as cotton plants, with increased expression of sucrose synthase as described in WO 02/45485;

e) plants, such as cotton plants, wherein the timing of the plasmodesmatal gating at the basis of the fibre cell is altered, e.g. through downregulation of fibre-selective β-1, 3-glucanase as described in WO 2005/017157;

f) plants, such as cotton plants, which have fibres with altered reactivity, e.g. through the expression of the N-acetylglucosaminetransferase gene, including nodC, and of chitin synthase genes as described in WO 2006/136351.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation impairing such altered oil characteristics and include:

a) plants, such as oilseed rape plants, which produce oil having a high oleic acid content as described e.g. in U.S. Pat. Nos. 5,969,169, 5,840,946 or 6,323,392 or 6,063,947;

b) plants, such as oilseed rape plants, which produce oil having a low linolenic acid content as described in U.S. Pat. Nos. 6,270,828, 6,169,190 or 5,965,755;

c) plants, such as oilseed rape plants, which produce oil having a low level of saturated fatty acids as described e.g. in U.S. Pat. No. 5,434,283.

Particularly useful transgenic plants which may be treated according to the invention are plants which comprise one or more genes which encode one or more toxins and are the following which are sold under the trade names YIELD GARD® (for example maize, cotton, soybeans), KnockOut® (for example maize), BiteGard® (for example maize), BT-Xtra@ (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soybean varieties which are sold under the trade names Roundup Ready® (tolerance to glyphosate, for example maize, cotton, soybean), Liberty Link® (tolerance to phosphinotricin, for example oilseed rape), IMI® (tolerance to imidazolinones) and SCS® (tolerance to sulphonylureas), for example maize. Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, that are listed for example in the databases from various national or regional regulatory agencies (see for example http://gmoinfo.jrc.it/gmp_browse.aspx and http://www.agbios.com/dbase.php).

Preferred sulphoximines of the general formula (I) for this application on transgenic plants and transgenic seed are:

(I-1), N-[6-chloropyridin-3-yl]methyl](methyl)oxido-$\lambda^4$-sulphanylidenecyanamide
(I-2), N-[6-trifluoromethylpyridin-3-yl]methyl](methyl)oxido-$\lambda^4$-sulphanylidenecyanamide
(I-3), N-methyl(oxido) [2-chloro-1,3-thiazol-5-yl]methyl] $\lambda^4$-sulphanylidenecyanamide
(I-4), N-methyl(oxido){[2-(trifluoromethyl)-1,3-thiazol-5-yl]methyl}$\lambda$-4-sulphanylidenecyanamide
(I-5), N-[6-chloropyridin-3-yl]ethyl](methyl)oxido-$\lambda^4$-sulphanylidenecyanamide
(I-6), N-[6-chloropyridin-3-yl]ethyl](methyl)oxido-$\lambda^4$-sulphanylidenecyanamide diastereomer
(I-7), N-[6-chloropyridin-3-yl]ethyl](methyl)oxido-$\lambda^4$-sulphanylidenecyanamide diastereomer
(I-8), N-[6-trifluoromethylpyridin-3-yl]ethyl](methyl)oxido-$\lambda^4$-sulphanylidenecyanamide
(I-9), N-[6-(1,1-difluoroethyl)pyrid-3-yl]ethyl](methyl)oxido-$\lambda^4$-sulphanylidenecyanamide
(I-10), N-[6-difluoromethylpyrid-3-yl]ethyl](methyl)oxido-$\lambda^4$-sulphanylidenecyanamide
(I-11), N-methyl(oxido) {1-[2-(trichloromethyl)pyrid-3-yl]ethyl}-$\lambda^4$-sulphanylidenecyanamide
(I-12), N-methyl(oxido) {1-[2-(pentafluoroethyl)pyrid-3-yl]ethyl}-$\lambda^4$-sulphanylidenecyanamide
(I-13), N-[6-chlorodifluoromethylpyrid-3-yl]ethyl](methyl)oxido-$\lambda^4$-sulphanylidenecyanamide
(I-14), N-methyl(oxido) {1-[2-(trifluoromethyl)-1,3-thiazol-5-yl]ethyl}-$\lambda^4$-sulphanylidenecyanamide
(I-15), N-methyl(oxido){1-[6-(trifluoromethyl)pyridin-3-yl]cyclopropyl-$\lambda^4$-sulphanylidenecyanamide
(I-16), N-methyl(oxido){1-(6-chloropyridin-3-yl)cyclopropyl-$\lambda^4$-sulphanylidenecyanamide
(I-17), N-2-(6-chloropyridin-3-yl)-1-oxidotetrahydro-1H-1$\lambda^4$-thienylidenecyanamide
(I-18), N-2-(6-trifluoromethylpyridin-3-yl)-1-oxidotetrahydro-1H-1$\lambda^4$-thienylidenecyanamide
(I-19), N-1-oxo-2-(2-trifluoromethyl-1,3-thiazol-5-ylmethyl)tetrahydro-1-$\lambda^6$-thiophen-1-ylidenecyanamide
(I-20), N-1-oxo-2-(6-trifluoromethylpyrid-3-ylmethyl)tetrahydro-1-$\lambda^6$-thiophen-1-ylidenecyanamide
(I-21), N-1-oxo-2-(6-chloropyrid-3-ylmethyl)tetrahydro-1-$\lambda^6$-thiophen-1-ylidenecyanamide
(I-22), N-1-oxo-2-(6-chloropyrid-3-ylmethyl)tetrahydro-1-$\lambda^6$-thiophen-1-ylidenecyanamide diastereomer
(I-23), N-1-oxo-2-(6-chloropyrid-3-ylmethyl)tetrahydro-1-$\lambda^6$-thiophen-1-ylidenecyanamide diastereomer Especially preferred sulphoximines of the general formula (I) for this application are:
(I-1), N-[6-chloropyridin-3-yl]methyl](methyl)oxido-$\lambda^4$-sulphanylidenecyanamide,
(I-2), N-[6-trifluoromethylpyridin-3-yl]methyl](methyl)oxido-$\lambda^4$-sulphanylidenecyanamide,
(I-3), N-methyl(oxido){[2-chloro-1,3-thiazol-5-yl]methyl}-$\lambda^4$-sulphanylidenecyanamide,
(I-4), N-methyl(oxido){[2-(trifluoromethyl)-1,3-thiazol-5-yl]methyl}-$\lambda^4$-sulphanylidenecyanamide,
(I-5), N-[6-chloropyridin-3-yl]ethyl](methyl)oxido-$\lambda^4$-sulphanylidenecyanamide,
(I-6), N-[6-chloropyridin-3-yl]ethyl](methyl)oxido-$\lambda^4$-sulphanylidenecyanamide diastereomer,
(I-7), N-[6-chloropyridin-3-yl]ethyl](methyl)oxido-$\lambda^4$-sulphanylidenecyanamide diastereomer,
(I-8), N-[6-trifluoromethylpyridin-3-yl]ethyl](methyl)oxido-$\lambda^4$-sulphanylidenecyanamide,
(I-14), N-methyl(oxido){1-[2-(trifluoromethyl)-1,3-thiazol-5-yl]ethyl}-$\lambda^4$-sulphanylidenecyanamide,
(I-15), N-methyl(oxido){1-[6-(trifluoromethyl)pyridin-3-yl]cyclopropyl-$\lambda^4$-sulphanylidenecyanamide,
(I-16), N-methyl(oxido) {1-(6-chloropyridin-3-yl)cyclopropyl-$\lambda^4$-sulphanylidenecyanamide Very especially preferred sulphoximines of the formula (I) for this application are:
(I-5), N-[6-chloropyridin-3-yl]ethyl](methyl)oxido-$\lambda^4$-sulphanylidenecyanamide,
(I-6), N-[6-chloropyridin-3-yl]ethyl](methyl)oxido-$\lambda^4$-sulphanylidenecyanamide diastereomer,
(I-7), N-[6-chloropyridin-3-yl]ethyl](methyl)oxido-$\lambda^4$-sulphanylidenecyanamide diastereomer,
(I-8), N-[6-trifluoromethylpyridin-3-yl]ethyl](methyl)oxido-$\lambda^4$-sulphanylidenecyanamide,
(I-15), N-methyl(oxido){1-[6-(trifluoromethyl)pyridin-3-yl]cyclopropyl-$\lambda^4$-sulphanylidenecyanamide,
(I-16), N-methyl(oxido) {1-(6-chloropyridin-3-yl)cyclopropyl-$\lambda^4$-sulphanylidenecyanamide, Within the scope of the present invention, the defence against the following pathogens is preferably enhanced: *Botrytis cinerea*, *Phytophthora nicotianae*, *Peronospora tabacinae*, *Phytophthora infestans*, *Sphaerotheca fuliginea*, *Phakopsora pachyrhizi*, *Ramularia gossypii*, *Rhizoctonia solani*, *Curvularia* spec., *Pyrenophora* spec., *Sclerotinia homoeocarpa*, *Erysiphe graminis*, *Colletotrichum graminicola*, *Pythium ultimum*, *Pythium aphanidermatum*.

Some pathogens which cause fungal and bacterial diseases and which come under the abovementioned generic terms may be mentioned by way of example, but not by limitation:
diseases caused by pathogens causing powdery mildew such as, for example,
*Blumeria* species such as, for example, *Blumeria graminis;*
*Podosphaera* species such as, for example, *Podosphaera leucotricha;*
*Sphaerotheca* species such as, for example, *Sphaerotheca fuliginea;*
*Uncinula* species such as, for example, *Uncinula necator;*
diseases caused by pathogens causing rust diseases such as, for example,
*Gymnosporangium* species such as, for example, *Gymnosporangium sabinae* Hemileia species such as, for example, *Hemileia vastatrix;*
*Phakopsora* species such as, for example, *Phakopsora pachyrhizi* and *Phakopsora meibomiae;*
*Puccinia* species such as, for example, *Puccinia recondita;*
*Uromyces* species such as, for example, *Uromyces appendiculatus;*
diseases caused by pathogens from the Oomycetes group such as, for example,
*Bremia* species such as, for example, *Bremia lactucae;*
*Peronospora* species such as, for example, *Peronospora pisi* or *P. brassicae;*
*Phytophthora* species such as, for example, *Phytophthora infestans;*
*Plasmopara* species such as, for example, *Plasmopara viticola;*
*Pseudoperonospora* species such as, for example, *Pseudoperonospora humuli* or *Pseudoperonospora cubensis;*
*Pythium* species such as, for example, *Pythium ultimum;*
leaf spot diseases and foliar wilts caused by, for example,

*Alternaria* species such as, for example, *Alternaria solani;*
*Cercospora* species such as, for example, *Cercospora beticola;*
*Cladiosporum* species such as, for example, *Cladiosporium cucumerinum;*
*Cochliobolus* species such as, for example, *Cochliobolus sativus* (conidial form: *Drechslera*, syn: *Helminthosporium*);
*Colletotrichum* species such as, for example, *Colletotrichum lindemuthanium;*
*Cycloconium* species such as, for example, *Cycloconium oleaginum;*
*Diaporthe* species such as, for example, *Diaporthe citri;*
*Elsinoe* species such as, for example, *Elsinoe fawcettii;*
*Gloeosporium* species such as, for example, *Gloeosporium laeticolor;*
*Glomerella* species such as, for example, *Glomerella cingulata;*
*Guignardia* species such as, for example, *Guignardia bidwelli;*
*Leptosphaeria* species such as, for example, *Leptosphaeria maculans;*
*Magnaporthe* species such as, for example, *Magnaporthe grisea;*
*Mycosphaerella* species such as, for example, *Mycosphaerella graminicola* and *Mycosphaerella fijiensis;*
*Phaeosphaeria* species such as, for example, *Phaeosphaeria nodorum;*
*Pyrenophora* species such as, for example, *Pyrenophora teres;*
*Ramularia* species such as, for example, *Ramularia collo-cygni;*
*Rhynchosporium* species such as, for example, *Rhynchosporium secalis;*
*Septoria* species such as, for example, *Septoria apii;*
*Typhula* species such as, for example, *Typhula incarnata;*
*Venturia* species such as, for example, *Venturia inaequalis;* root and stem diseases caused by, for example,
*Corticium* species such as, for example, *Corticium graminearum;*
*Fusarium* species such as, for example, *Fusarium oxysporum;*
*Gaeumannomyces* species such as, for example, *Gaeumannomyces graminis;*
*Rhizoctonia* species such as, for example, *Rhizoctonia solani;*
*Tapesia* species such as, for example, *Tapesia acuformis;*
*Thielaviopsis* species such as, for example, *Thielaviopsis basicola;* ear and panicle diseases (including maize cobs), caused by, for example,
*Alternaria* species such as, for example, *Alternaria* spp.;
*Aspergillus* species such as, for example, *Aspergillus flavus;*
*Cladosporium* species such as, for example, *Cladosporium* spp.;
*Claviceps* species such as, for example, *Claviceps purpurea;*
*Fusarium* species such as, for example, *Fusarium culmorum;*
*Gibberella* species such as, for example, *Gibberella zeae;*
*Monographella* species such as, for example, *Monographella nivalis;* diseases caused by smuts such as, for example,
*Sphacelotheca* species such as, for example, *Sphacelotheca reiliana;*
*Tilletia* species such as, for example, *Tilletia caries;*
*Urocystis* species such as, for example, *Urocystis occulta;*
*Ustilago* species such as, for example, *Ustilago nuda;* fruit rot caused by, for example,
*Aspergillus* species such as, for example, *Aspergillus flavus;*
*Botrytis* species such as, for example, *Botrytis cinerea;*
*Penicillium* species such as, for example, *Penicillium expansum* and *Penicillium purpurogenum;*
*Sclerotinia* species such as, for example, *Sclerotinia sclerotiorum;*
*Verticilium* species such as, for example, *Verticilium alboatrum;* seed- and soil-borne rots and wilts, and seedling diseases, caused by, for example,
*Alternaria* species such as, for example, *Alternaria brassicicola;*
*Aphanomyces* species such as, for example, *Aphanomyces euteiches;*
*Ascochyta* species such as, for example, *Ascochyta lentis;*
*Aspergillus* species such as, for example, *Aspergillus flavus;*
*Cladosporium* species such as, for example, *Cladosporium herbanim;*
*Cochliobolus* species such as, for example, *Cochliobolus sativus;* (conidial form: *Drechslera, Bipolaris* syn: *Helminthosporium*);
*Colletotrichum* species such as, for example, *Colletotrichum coccodes;*
*Fusarium* species such as, for example, *Fusarium culmorum;*
*Gibberella* species such as, for example, *Gibberella zeae;*
*Macrophomina* species such as, for example, *Macrophomina phaseolina;*
*Monographella* species such as, for example, *Monographella nivalis;*
*Penicillium* species such as, for example, *Penicillium expansum;*
*Phoma* species such as, for example, *Phoma lingam;*
*Phomopsis* species such as, for example, *Phomopsis sojae;*
*Phytophthora* species such as, for example, *Phytophthora cactorum;*
*Pyrenophora* species such as, for example, *Pyrenophora graminea;*
*Pyricularia* species such as, for example, *Pyricularia oryzae;*
*Pythium* species such as, for example, *Pythium ultimum;*
*Rhizoctonia* species such as, for example, *Rhizoctonia solani;*
*Rhizopus* species such as, for example, *Rhizopus oryzae;*
*Sclerotium* species such as, for example, *Sclerotium rolfsii;*
*Septoria* species such as, for example, *Septoria nodorum;*
*Typhula* species such as, for example, *Typhula incarnata;*
*Verticillium* species such as, for example, *Verticillium dahliae;* cankers, galls and witches' brooms, caused by, for example,
  *Nectria* species such as, for example, *Nectria galligena;*
wilts caused by, for example,
  *Monilinia* species such as, for example, *Monilinia laxa;*
deformations of leaves, flowers and fruits, caused by, for example,
  *Taphrina* species such as, for example, *Taphrina deformans;*
degenerative diseases of woody species, caused by, for example,
  *Esca* species such as, for example, *Phaemoniella clamydospora* and *Phaeoacremonium aleophilum* and *Fomitiporia mediterranea;*
flower and seed diseases caused by, for example,
  *Botrytis* species such as, for example, *Botrytis cinerea;*
diseases of plant tubers caused by, for example,
  *Rhizoctonia* species such as, for example, *Rhizoctonia solani;*
  *Helminthosporium* species such as, for example, *Helminthosporium solani;*
diseases caused by bacterial pathogens such as, for example,
  *Xanthomonas* species such as, for example, *Xanthomonas campestris* pv. *oryzae; Pseudomonas* species such as, for example, *Pseudomonas syringae* pv. *lachrymans; Erwinia* species such as, for example, *Erwinia amylovora;*

The following diseases of soybeans can preferably be controlled:
fungal diseases on leaves, stems, pods and seeds caused by, for example,
alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*)
fungal diseases on roots and at the stem base caused by, for example,
black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Preferred points in time for the application of sulphoximines for the purposes of pathogen defence are treatments of the seed, the soil, the nutrient solutions, the stems and/or the leaves with the approved application rates.

In order to achieve the properties according to the invention, the amounts of sulphoximine can be varied within a substantial range. To achive an effect, it is preferred to use concentrations of from 0.00001% to 0.05%, especially preferably of from 0.000025% to 0.025% and very especially preferably of from 0.000025% to 0.005%. When mixtures are employed, the concentration of the active substance combinations is preferably between 0.000025% and 0.005%, especially preferably between 0.00005% and 0.001%. The data given hereinbelow and hereafter are, unless otherwise specified, percent by weight.

To enhance plants' intrinsic defences and/or to improve plant growth and/or to increase the resistance of plants to plant diseases, the active substances according to the invention may also be employed in the treatment of seed. Active substances to be mentioned by preference in this context are in particular those mentioned above as being preferred, especially preferred and very especially preferred. In this respect, the compounds of the general formulae (Ia) to (Ik) and the specific compounds of the formulae (I-1) to (I-23) must be mentioned in particular.

The majority of the damage caused on crop plants is generated as early as during the seed state during storage and after the seed has been introduced into the soil, and during and immediately after the gemination of the plants. This phase is particularly critical since the roots and shoots of the grown plant are especially sensitive, and even a small amount of damage can lead to the dying of the whole plant. There exists, therefore, a great deal of interest in enhancing the plants' intrinsic defences of the seed, in supporting plant growth, in increasing the resistance of the seed and of the seedling to plant diseases, in other words, therefore, in protecting the germinating plant by using suitable means.

The treatment of the seed of plants has been known for a long time and is the subject of continuous improvement. However, the treatment of seed poses a series of problems which cannot always be solved in a satisfactory manner. Thus, it is desirable to develop methods of protecting the seed and the germinating plant which dispense with the additional application of plant protection compositions or of compositions for improving plant growth and for increasing the resistance of plants to plant diseases, which are caused by fungi, bacteria, viruses, MLOs and/or RLOs, after sowing or after the emergence of the plants. It is furthermore desirable to optimize the amount of the active substance employed in such a way as to provide the best possible protection for the seed and the germinating plant without, however, damaging the plant itself by the active substance employed.

The present invention therefore especially also relates to a method of protecting seed and germinating plants for improving plant growth and/or for increasing the resistance of plants to plant diseases, which are caused by fungi, bacteria, viruses, MLOs and/or RLOs, by treating the seed and/or the germinating plant with an active substance according to the invention. The invention also relates to the corresponding use of the active substances according to the invention for the treatment of seed. The invention furthermore relates to seed which has been treated with an active substance according to the invention.

Moreover, the present invention also relates to corresponding nutrient solutions, in particular for growing plants and/or germinating plants, comprising an amount of at least one sulphoximine, in particular of a sulphoximine of the general formula (I), which is effective for increasing plants' intrinsic defences and/or for improving plant growth and/or for increasing the resistance of plants to plant diseases caused by fungi, bacteria, viruses, MLOs (mycoplasma-like organisms) and/or RLOs (rickettsia-like organisms). In this context, the nutrient solutions preferably contain the at least one sulphoximine in an amount of from 0.0005 to 0.025% by weight, based on the total weight of the nutrient solution. In preferred embodiments, the at least one sulphoximine is present in the form of an NMP-free formulation comprising 10 to 50% by weight of propylene carbonate.

In a preferred embodiment, the method of protecting seed and germinating plants for improving plant growth and/or for increasing the resistance of plants to plant diseases, which are caused by fungi, bacteria, viruses, MLOs and/or RLOs is carried out by growing the seed together with an active substance according to the invention in what is known as the float method or floating method (Leal, R. S., The use of Confidor S in the float, a new tobacco seedlings production system in the South of Brazil Pflanzenschutz-Nachrichten Bayer (German edition) (2001), 54(3), pages 337 to 352; Rudolph, R. D.; Rogers, W. D.; The efficacy of imidacloprid treatment for reduction in the severity of insect vectored virus diseases of tobacco. Pflanzenschutz-Nachrichten Bayer (German edition) (2001), 54(3), pages 311 to 336). In this method, the seed is sown in specific containers, for example perforated Styropor trays, in specific seed compost based on peat medium, and subsequently cultured in containers with a suitable nutrient solution until the desired transplant size has been reached (cf. FIG. 1). Here, the containers are allowed to float on the nutrient solution, which gives the cultivation method its name (Leal, 2001, see above). In floating methods, insecticides from the neonicotinoid (chloronicotinyl) class have been employed for some years for controlling certain insects.

The floating method is explained in greater detail with the aid of the appended FIGS. 1 to 3.

It is one of the advantages of the present invention that, due to the particular systemic properties of the active substances according to the invention, the treatment of the seed with these active substances protects not only the seed itself, but also the plants which it generates after emergence in such a way that the growth of the plants is enhanced and the resistance of plants to plant diseases caused by fungi, bacteria, viruses, MLOs and/or RLOs is increased. Thus, the direct treatment of the crop at the point of sowing or shortly thereafter can be dispensed with.

Another advantage is that the mixtures according to the invention can also be employed in particular for transgenic seed.

The compositions according to the invention are suitable for the protection and support of seed of any plant variety as already mentioned above which is employed in agriculture, in the greenhouse, in afforestation or in horticulture. In particular, this takes the form of seed of maize, peanut, canola, oilseed rape, poppy, soya, cotton, beet (for example sugar beet and fodder beet), rice, sorghum and millet, wheat, barley, oats, rye, sunflower, tobacco, potatoes or vegetables (for example tomatoes, brassicas). The active substances to be used according to the invention are also suitable for the treatment of the seed of fruit plants or vegetables. Particularly important is the treatment of the seed of maize, soya, cotton, wheat and canola or oilseed rape.

As already mentioned above, the treatment of transgenic seed with a composition according to the invention is also particularly important.

Within the scope of the present invention, the active substances according to the invention are applied to the seed either alone or in the form of a suitable foi mlation. The seed is preferably treated in a state in which it is sufficiently stable to avoid damage during the treatment. In general, treatment of the seed can be effected at any point in time between harvest and sowing. Usually, seed is used which has been separated from the plant and freed from cobs, hulls, stems, coats, hair or pulp.

When treating seed, care must be taken generally that the amount of the active substances according to the invention and/or further additives which is/are applied to the seed is chosen in such a way that the germination of the seed is not adversely affected, or the plant which the seed gives rise to is not damaged. This is in particular the case for active substances which may have phytotoxic effects at certain application rates.

The compositions according to the invention can be applied directly, which means without comprising further components and without having been diluted. As a rule, it is preferable to apply the compositions to the seed in the form of a suitable formulation. Suitable formulations and methods for the treatment of seed are known to the skilled worker and are described, for example, in the following documents: U.S. Pat. Nos. 4,272,417 A, 4,245,432 A, 4,808,430 A, 5,876,739 A, US 2003/0176428 A1, WO 2002/080675 A1, WO 2002/028186 A2.

The active substances which can be used in accordance with the invention can be converted into the customary seed-dressing formulations, such as solutions, emulsions, suspensions, powders, foams, slurries or other coating compositions for seed, and ULV formulations.

These formulations are prepared in a known manner by mixing the active substances according to the invention with customary additives such as, for example, customary extenders and solvents or diluents, colorants, wetters, dispersants, emulsifiers, antifoams, preservatives, secondary thickeners, adhesives, gibberellins, and also water.

Colorants which may be present in the seed-dressing formulations which can be used in accordance with the invention are all colorants which are customary for such purposes. In this context, not only pigments, which are sparingly soluble in water, but also dyes, which are soluble in water, may be used. Examples which may be mentioned are the colorants known as Rhodamin B, C.I. Pigment Red 112 and C.I. Solvent Red 1.

Wetters which may be present in the seed-dressing formulations which can be used in accordance with the invention are all those substances which promote wetting and which are customary in the formulation of agrochemical active substances. The following can preferably be used: alkylnaphthalene sulphonates, such as diisopropyl- or diisobutylnaphthalene sulphonates.

Dispersants and/or emulsifiers which may be present in the seed-dressing formulations which can be used in accordance with the invention are all those nonionic, anionic and cationic dispersants which are customary in the formulation of agrochemical active substances. The following can preferably be used: nonionic or anionic dispersants or mixtures of nonionic or anionic dispersants. Suitable nonionic dispersants are, in particular, ethylene oxide/propylene oxide block polymers, alkylphenol polyglycol ethers and tristryrylphenol polyglycol ether, and their phosphated or sulphated derivatives. Suitable inorganic dispersants are, in particular, lignosulphonates, polyacrylic acid salts and arylsulphonate/formaldehyde condensates.

Antifoams which can be used in the seed-dressing formulations which can be used in accordance with the invention are all those foam-inhibitory substances which are customary in the formulations of agrochemical active substances. Silicone antifoams and magnesium stearate can preferably be used.

Preservatives which can be used in the seed-dressing formulations which can be used in accordance with the invention are all substances which can be used for such purposes in agrochemical compositions. Examples which may be mentioned are dichlorophene and benzyl alcohol hemiformal.

Secondary thickeners which can be used in the seed-dressing formulations which can be used in accordance with the invention are all substances which can be used for such purposes in agrochemical compositions. The following are preferably suitable: cellulose derivatives, acrylic acid derivatives, xanthan, modified clays and highly-disperse silica.

Adhesives which may be present in the seed-dressing formulations which can be used in accordance with the invention are all customary binders which can be employed in seed-dressing products. The following may be mentioned by preference: polyvinylpyrrolidone, polyvinyl acetate, polyvinyl alcohol and tylose.

Gibberellins which may be present in the seed-dressing formulations which can be used in accordance with the invention are preferably the gibberellins A1, A3 (=gibberellic acid), A4 and A7, with gibberellic acid being especially preferably used. The gibberellins are known (cf. R. Wegler "Chemie der Pflanzenschutz- and Schädlingsbekampfungsmittel" [Chemistry of Crop Protectants and Pesticides], Vol. 2, Springer Verlag, 1970, p. 401-412).

The seed-dressing formulations which can be used for the treatment of a wide range of seed, including the seed of transgenic plants, in accordance with the invention can be employed either directly or after previously having been diluted with water.

All mixing apparatuses which can be employed for dressing seed are suitable for treating seed with the seed-dressing formulations which can be used in accordance with the invention or the preparations prepared therefrom by addition of water. Specifically, a procedure is followed for the seed-dressing process in which the seed is introduced into a mixer, the specific required amount of seed-dressing formulation, either as such or after having previously been diluted with water, is added, and everything is mixed until the formulation has been distributed uniformly on the seed. If appropriate, this is followed by a drying process.

In general, the active substances according to the invention may additionally be present, in their commercially available formulations and in the use forms prepared from these formulations, as mixtures with other active substances, such as insecticides, attractants, sterilants, acaricides, nematicides, fungicides, growth-regulating substances or herbicides.
Fungicides:
(1) Nucleic acid synthesis inhibitors, such as, for example, benalaxyl, benalaxyl-M, bupirimate, clozylacon, dimethirimol, ethirimol, furalaxyl, hymexazol, metalaxyl, metalaxyl-M, ofurace, oxadixyl and oxolinic acid.
(2) Mitosis and cell division inhibitors, such as, for example, benomyl, carbendazim, chlorfenazole, diethofencarb, ethaboxam, fuberidazole, pencycuron, thiabendazole, thiophanate, thiophanate-methyl and zoxamide.
(3) Respiration inhibitors (respiratory chain inhibitors), such as, for example, diflumetorim as inhibitor at complex I of the respiratory chain; bixafen, boscalid, carboxin, fenfuram, flutolanil, fluopyram, furametpyr, furmecyclox, isopyrazam (mixture of the syn-epimeric racemate 1RS, 4SR,9RS and the anti-epimeric racemate 1RS,4SR,9SR), isopyrazam (syn-epimeric racemate 1RS,4SR,9RS), isopyrazam (syn-epimeric enantiomer 1R,4S,9R), isopyrazam (syn-epimerc enantiomer 1S,4R,9S), isopyrazam (anti-epimeric racemate 1RS,4SR,9SR), isopyrazam (anti-epimeric enantiomer 1R,4S,9S), isopyrazam (anti-epimeric enantiomer 1S,4R,9R), mepronil, oxycarboxin, penflufen, penthiopyrad, sedaxane, thifluzamide as inhibitors at complex II of the respiratory chain; amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyraoxystrobin, pyrametostrobin, pyribencarb, trifloxystrobin as inhibitors at complex III of the respiratory chain.
(4) Decouplers, such as, for example, binapacryl, dinocap, fluazinam and meptyldinocap.
(5) ATP production inhibitors, such as, for example, fentin acetate, fentin chloride, fentin hydroxide and silthiofam.
(6) Amino acid and protein biosynthesis inhibitors, such as, for example, andoprim, blasticidin-S, cyprodinil, kasugamycin, kasugamycin hydrochloride hydrate, mepanipyrim and pyrimethanil.
(7) Signal transduction inhibitors, such as, for example, fenpiclonil, fludioxonil and quinoxyfen.
(8) Lipid and membrane synthesis inhibitors, such as, for example, biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl and vinclozolin.
(9) Ergosterol biosynthesis inhibitors, such as, for example, aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidole, flusilazole, flutriafol, furconazole, furconazole-cis, hexaconazole, imazalil, imazalil sulphate, imibenconazole, ipconazole, metconazole, myclobutanil, naftifin, nuarimol, oxpoconazole, paclobutrazole, pefurazoate, penconazole, piperalin, prochloraz, propiconazole, prothioconazole, pyributicarb, pyrifenox, quinconazole, simeconazole, spiroxamine, tebuconazole, terbinafin, tetraconazole, triadimefon, triadimenol, tridemorph, triflumizole, triforin, triticonazole, uniconazole, viniconazole and voriconazole.
(10) Cell wall synthesis inhibitors, such as, for example, benthiavalicarb, dimethomorph, flumorph, iprovalicarb, mandipropamide, polyoxins, polyoxorim, prothiocarb, validamycin A and valefenalate.
(11) Melanin biosynthesis inhibitors, such as, for example, carpropamid, diclocymet, fenoxanil, fthalide, pyroquilon and tricyclazole.
(12) Resistance inductors such as, for example, acibenzolar-5-methyl, probenazole and tiadinil.
(13) Compounds with multisite activity such as, for example, Bordeaux mixture, captafol, captan, chlorothalonil, copper naphthenate, copper oxide, copper oxychloride, copper preparations such as copper hydroxide, copper sulphate, dichlofluanid, dithianone, dodine and its free base, ferbam, fluorofolpet, folpet, guazatine, guazatine acetate, iminoctadine, iminoctadine albesilate, iminoctadine triacetate, mancopper, mancozeb, maneb, metiram, zinc metiram, copper oxine, propamidin, propineb, sulphur and sulphur preparations such as, for example, calcium polysulphide, thiram, tolylfluanid, zineb and ziram.
(14) Other compounds such as, for example, 2,3-dibutyl-6-chlorothieno[2,3-d]pyrimidin-4(3H)-one, ethyl (2Z)-3-amino-2-cyano-3-phenylprop-2-enoate, N-[2-(1,3-dimethylbutyl)phenyl]-5-fluoro-1,3-dimethyl-1H-pyrazole-4-carboxamide, 3-(difluoromethyl)-1-methyl-N-(3',4',5'- trifluorobiphenyl-2-yl)-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, (2E)-2-(2-[6-(3-chloro-2-methylphenoxy)-5-fluoropyrimidin-4-yl]oxy]phenyl)-2-(methoxyimino)-N-methylethanamide, (2E)-2-{24 {[(2E,3E)-4-(2,6-dichlorophenyl)but-3-en-2-ylidene]amino]oxy)methyl] phenyl]-2-(methoxyimino)-N-methylethanamide, 2-chloro-N-(1,1,3-trimethyl-2,3-dihydro-1H-inden-4-yl) pyridine-3-carboxamide, N-(3-ethyl-3,5,5-trimethylcyclohexyl)-3-(formylamino)-2-hydroxybenzamide, 5-methoxy-2-methyl-4-(2-{[({(1E)-143-(trifluoromethyl) phenyl]ethylidene}amino)oxy]methyl}phenyl)-2,4-dihydro-3H-1,2,4-triazol-3-one, (2E)-2-(methoxyimino)-N-methyl-2-(2-{[({(1E)-143-(trifluoromethyl)phenyl]-ethylidene}amino)oxy]methyl}phenyl)ethanamide, (2E)-2-(methoxyimino)-N-methyl-2-{2-[(E)-({1-[3-(trifluoromethyl)phenyl]ethoxy imino)methyl] phenyl}ethanamide, (2E)-2-{2-[([(1E)-1-(3-[(E)-1-fluoro-2-phenylethenyl]oxy)phenyl)ethylidene] amino}oxy)methyl]phenyl}-2-(methoxyimino)-N-methylethanamide, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylic acid, N-ethyl-N-methyl-N'-{2-methyl-5-(trifluoromethyl)-4-[3-(trimethylsilyl)propoxy]phenyl}imidoformamide, N'-{5-(difluoromethyl)-2-methyl-4-[3-(trimethylsilyl) propoxy]phenyl}-N-ethyl-N-methylimidoformamide, O-{1-[(4-methoxyphenoxy)methyl]-2,2-dimethylpropyl}1H-imidazole-1-carbothioate, N-[2-(4-{[3-(4-chlorophenyl)prop-2-yn-1-yl]oxy}-3-methoxyphenyl)ethyl]-N$^2$-(methylsulphonyl)valinamide, 5-chloro-7-(4-methylpiperidin-1-yl)-6-(2,4,6-trifluorophenyl) [1,2,4] triazolo[1,5-a]pyrimidine, 5-amino-1,3,4-thiadiazole-2-thiol, propamocarb-fosetyl, 1-[(4-methoxyphenoxy) methyl]-2,2-dimethylpropyl 1H-imidazole-1-carboxylate, 1-methyl-N-[2-(1,1,2,2-tetrafluoroethoxy)phenyl]-3-(trifluoromethyl)-1H-pyrazole-4-carboxamide, 2,3,5,6-tetrachloro-4-(methylsulphonyl)pyridine, 2-butoxy-6-iodo-3-propyl-4H-chromen-4-one, 2-phenylphenol and its salts, 3-(difluoromethyl)-1-methyl-N-[2-(1,1,2,2-tetrafluoroethoxy)phenyl]-1H-pyrazole-4-carboxamide, 3,4,5-trichloropyridin-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 8-hydroxyquinoline, 8-hydroxyquinoline sulphate, tebufloquin, 5-methyl-6-octyl-3,7-dihydro[1,2,4]triazolo[1,5-a]pyrimidine-7-amine, 5-ethyl-6-octyl-3,7-dihydro[1,2,4] triazolo[1,5-a]-pyrimidine-7-amine, ametoctradin, benthiazole, bethoxazin, capsimycin, carvone, quinomethionate, chloroneb, cufraneb, cyflufenamid, cymoxanil, cyprosulphamide, dazomet, debacarb, dichlorophen, diclomezin, dicloran, difenzoquat, difenzoquat methylsulphate, diphenylamine, ecomat, ferimzone, flumetover, fluopicolid, fluoromide, flusulfamide, flutianil, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl}-3-methoxyacrylate, methyl isothiocyanate, metrafenon, (5-chloro-2-methoxy-4-methylpyridin-3-yl)(2,3,4-trimethoxy-6-methylphenyl)methanone, mildiomycin, tolnifanid, N-(4-chlorobenzyl)-3-[3-methoxy-4-(prop-2-yn-1-yloxy) phenyl]propanamide, N-[(4-chlorophenyl)(cyano) methyl]-3-[3-methoxy-4-(prop-2-yn-1-yloxy)phenyl] propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl) ethyl]-2-fluoro-4-iodopyridine-3-carboxamide, N-{(Z)-[(cyclopropylmethoxy)imino][6-(difluoromethoxy)-2,3-difluorophenyl]methyl}-2-phenylacetamide, N-{(E)-[(cyclopropylmethoxy)imino][6-(difluoromethoxy)-2,3-difluorophenyl]methyl}-2-phenylacetamide, natamycin, nickel dimethyldithiocarbamate, nitrothal-isopropyl, octhilinone, oxamocarb, oxyfenthiin, pentachlorophenol and its salts, phenazin-1-carboxylic acid, phenothrin, phosphoric acid and its salts, propamocarb fosetylate, propanosine-sodium, proquinazid, pyrroInitrin, quintozene, S-prop-2-en-1-yl 5-amino-2-(1-methylethyl)-4-(2-methylphenyl)-3-oxo-2,3-dihydro-1H-pyrazole-1-carbothioate, tecloftalam, tecnazene, triazoxide, trichlamide, 5-chloro-N'-phenyl-N'-prop-2-yn-1-ylthiophene-2-sulphonohydrazide, zarilamid, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl) N-(1,2,3,4-tetrahydronaphthalen-1-yl)-1,3-thiazole-4-carboxamide, 3-(difluoromethyl)-N-[4-fluoro-2-(1,1,2,3,3,3-hexafluoropropoxy)phenyl]-1-methyl-1H-pyrazole-4-carboxamide and pentyl-{6-[({[(1-methyl-1H-tetrazol-5-yl)(phenyl)methylidene]amino}oxy)methyl]pyridin-2-yl}carbamate.

Bactericides:

Bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:

The active substances mentioned in the present description by their "common name" are known for example from "The Pesticide Manual" 14th Ed., British Crop Protection Council 2006 and from the website http://www.alanwood.net/pesticides.

(1) Acetylcholine esterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-5-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothio-phosphoryl) salicylate, isoxathione, malathion, mecarbam, methamidophos, methidathion, mevinphos, monocrotophos, naled, omethoate, oxydemeton-methyl, parathion (-methyl), phenthoate, phorate, phosal one, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triazamate, triclorfon and vamidothion.

(2) GABA-controlled chloride channel antagonists, such as, for example, organochlorines, for example chlordane and endosulfan (alpha-); or fiproles (phenylpyrazoles), for example ethiprole, fipronil, pyrafluprole and pyriprole.

(3) Sodium channel modulators/voltage-dependent sodium channel blockers, such as, for example, pyrethroids, for example acrinathrin, allethrin (d-cis-trans, d-trans), bifenthrin, bioallethrin, bioallethrin-5-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans isomers], deltamethrin, dimefluthrin, empenthrin [(EZ)-(1R) isomers], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans isomer], prallethrin, profluthrin, pyrethrine (pyrethrum), resmethrin, RU 15525, silafluofen, tefluthrin, tetramethrin [(1R) isomers], tralomethrin, transfluthrin and ZXI 8901; or DDT; or methoxychlor.

(4) Nicotinergic acetylcholine receptor agonists, such as, for example, neonicotinoids, for example acetamiprid, clothianidin, dinotefuran, imidacloprid, nitenpyram, thiacloprid, thiamethoxam; or nicotine.

(5) Allosteric acetylcholine receptor modulators (agonists), such as, for example, spinosyns, for example spinetoram and spinosad.

(6) Chloride channel activators, such as, for example, avermectins/milbemycins, for example abamectin, emamectin benzoate, lepimectin and milbemectin.

(7) Juvenile hormone analogues, for example hydroprene, kinoprene, methoprene; or fenoxycarb; pyriproxyfen.

(8) Active substances with unknown or unspecific mechanisms of action, such as, for example, fumigants, for example, methyl bromide and other alkyl halides; or chloropicrin; sulphuryl fluoride; borax; tartar emetic.

(9) Selective antifeedants, for example pymetrozine; or flonicamid.

(10) Mite growth inhibitors, for example clofentezine, diflovidazin, hexythiazox, etoxazole.

(11) Microbial disruptors of the insect gut membrane, such as, for example, *Bacillus thuringiensis* subsp. *israelensis*, *Bacillus sphaericus*, *Bacillus thuringiensis* subsp. *aizawai*, *Bacillus thuringiensis* subsp. *kurstaki*, *Bacillus thuringiensis* subsp. *tenebrionis*, and BT plant proteins, for example Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, such as, for example, diafenthiuron; or organotin compounds, for example azocyclotin, cyhexatin, fenbutatin oxide; or propargite; tetradifon.

(13) Decouplers of oxidative phosphorylation by interrupting the H proton gradient, such as, for example, chlorfenapyr and DNOC.

(14) Nicotinergic acetylcholine receptor antagonists, such as, for example, bensultap, cartap (-hydrochloride), thiocylam and thiosultap (-sodium).

(15) Chitin biosynthesis inhibitors, type 0, such as, for example, benzoylureas, for example bistrifluoron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, such as, for example, buprofezine.

(17) Moulting-disrupting active substances, such as, for example, cyromazine.

(18) Ecdysone agonists/disruptors, such as, for example, diacylhydrazines, for example chromafenozide, halofenozide, methoxyfenozide and tebufenozide.

(19) Octopaminergic agonists, such as, for example, amitraz.

(20) Site-III electron transport inhibitors/site-II electron transport inhibitors, such as, for example, hydramethylnon; acequinocyl; fluacrypyrim; or cyflumetofen and cyenopyrafen.

(21) Electron transport inhibitors, such as, for example, site-I electron transport inhibitors from the group of the METI acaricides, for example fenazaquin, fenpyroximate, pyrimidifen, pyridaben, tebufenpyrad, tolfenpyrad; or rotenone (Derris).

(22) Voltage-dependent sodium channel blockers, for example indoxacarb; metaflumizone.

(23) Acetyl-CoA carboxylase inhibitors, such as, for example, tetronic acid derivatives, for example spirodiclofen and spiromesifen; or tetramic acid derivatives, for example spirotetramat.

(24) Site-IV electron transport inhibitors, such as, for example, phosphines, for example aluminium phosphide, calcium phosphide, phosphine, zinc phosphide; or cyanide.

(28) Ryanodin receptor effectors, such as, for example diamides, for example chlorantraniliprole (rynaxypyr), cyantraniliprole (cyazypyr) and flubendiamide.

Further active substances with unknown mechanism of action, such as, for example, azadirachtin, amidoflumet, benzoximate, bifenazate, quinomethionate, cryolite, dicofol, flufenerim, pyridalyl and pyrifluquinazon; or the following known active compounds:

4-{[(6-bromopyrid-3-yl)methyl](2-fluoroethyl) amino}furan-2(5H)-one (disclosed in WO 2007/115644), 4-{[(6-fluoropyrid-3-yl)methyl](2,2-difluoroethyl) amino}furan-2(5H)-one (disclosed in WO 2007/115644), 4-{[(2-chloro-1,3-thiazol-5-yl)methyl](2-fluoroethyl)amino}-furan-2(5H)-one (disclosed in WO 2007/115644), 4-{[(6-chloropyrid-3-yl)methyl](2-fluoroethyl)amino}furan-2(5H)-one (disclosed in WO 2007/115644), 4-{[(6-chloropyrid-3-yl)methyl](2,2-difluoroethyl)amino}furan-2(5H)-one (disclosed in WO 2007/115644), 4-{[(6-chloro-5-fluoropyrid-3-yl)methyl](methyl)amino}furan-2(5H)-one (disclosed in WO 2007/115643), 4-{[(5,6-dichloropyrid-3-yl)methyl](2-fluoroethyl)amino}furan-2(5H)-one (disclosed in WO 2007/115646), 4-{[(6-chloro-5-fluoropyrid-3-yl)methyl](cyclopropyl)amino}furan-2(5H)-one (disclosed in WO 2007/115643), 4-{[(6-chloropyrid-3-yl)methyl](cyclopropyl)amino}furan-2(5H)-one (disclosed in EP-A-0 539 588), 4-{[(6-chloropyrid-3-yl)methyl](methyl)amino}furan-2(5H)-one (disclosed in EP-A-0 539 588), [(6-chloropyridin-3-yl)methyl](methyl)oxido-λ⁴-sulphanylidenecyanamide (disclosed in WO 2007/149134), [1-(6-chloropyridin-3-yl)ethyl](methyl)oxido-λ⁴-sulphanylidenecyanamide (disclosed in WO 2007/149134) and its diastereomers (A) and (B)

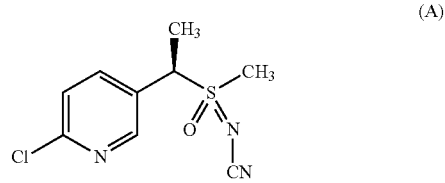

(A)

-continued

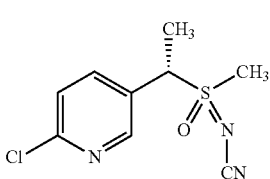

(B)

(likewise disclosed in WO 2007/149134), [(6-trifluoromethylpyridin-3-yl)methyl](methyl)oxido-$\lambda^4$-sulphanylidenecyanamide (disclosed in WO 2007/095229), sulfoxaflor (likewise disclosed in WO 2007/149134), 11-(4-chloro-2,6-dimethylphenyl)-12-hydroxy-1,4-dioxa-9-azadispiro[4.2.4.2]tetradec-11-en-10-one (disclosed in WO 2006/089633), 3-(4'-fluoro-2,4-dimethylbiphenyl-3-yl)-4-hydroxy-8-oxa-1-azaspiro[4.5]dec-3-en-2-one (disclosed in WO 2008/067911) and 1-{2,4-dimethyl-5-[(2,2,2-trifluoroethyl)sulphinyl]phenyl}-3-(trifluoromethyl)-1H-1,2,4-triazole (disclosed in WO 1999/55668).

Figure 1:
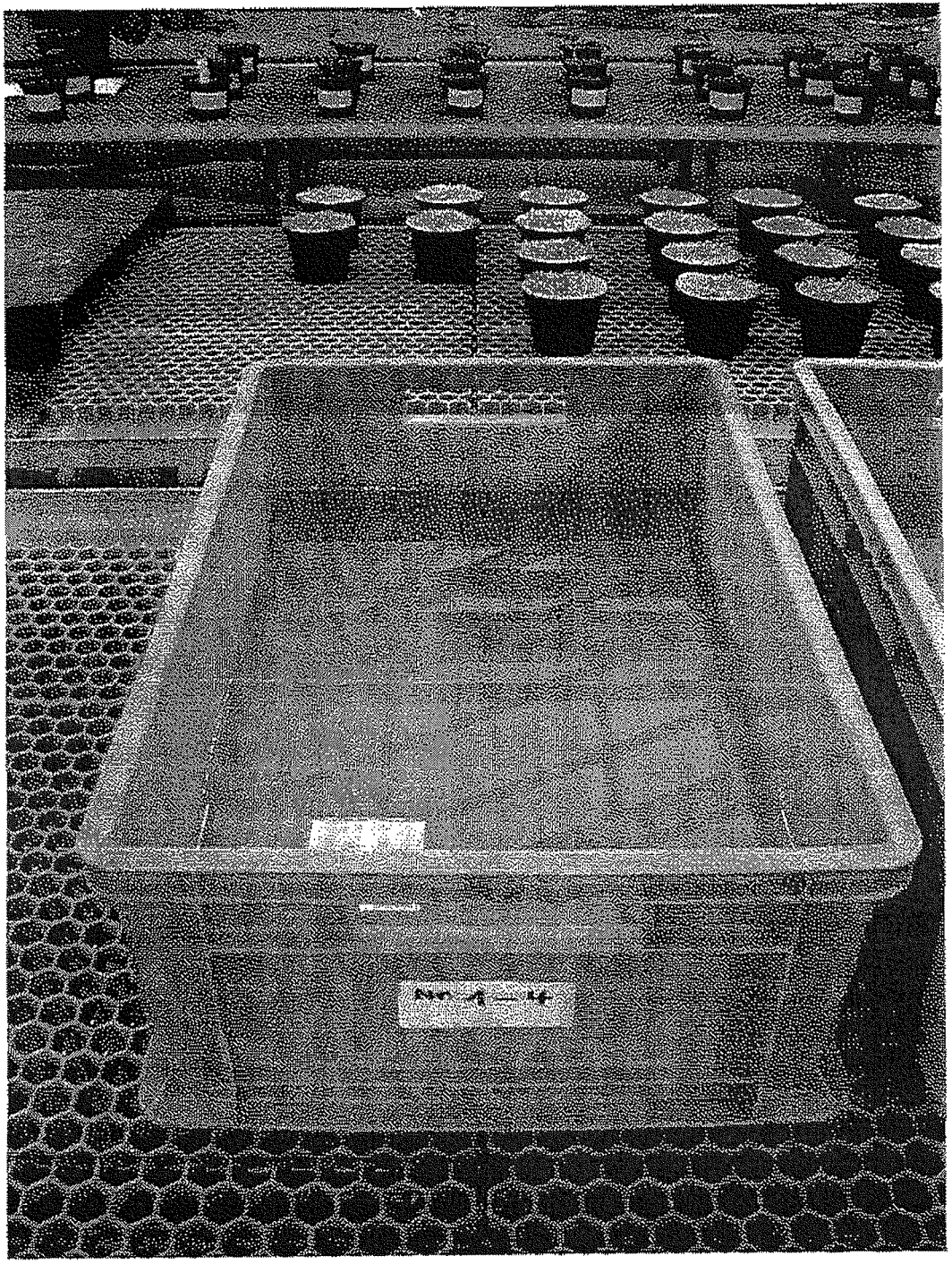
FIG. 1: Floating Box filled with nutrient solution.
Figure 2:
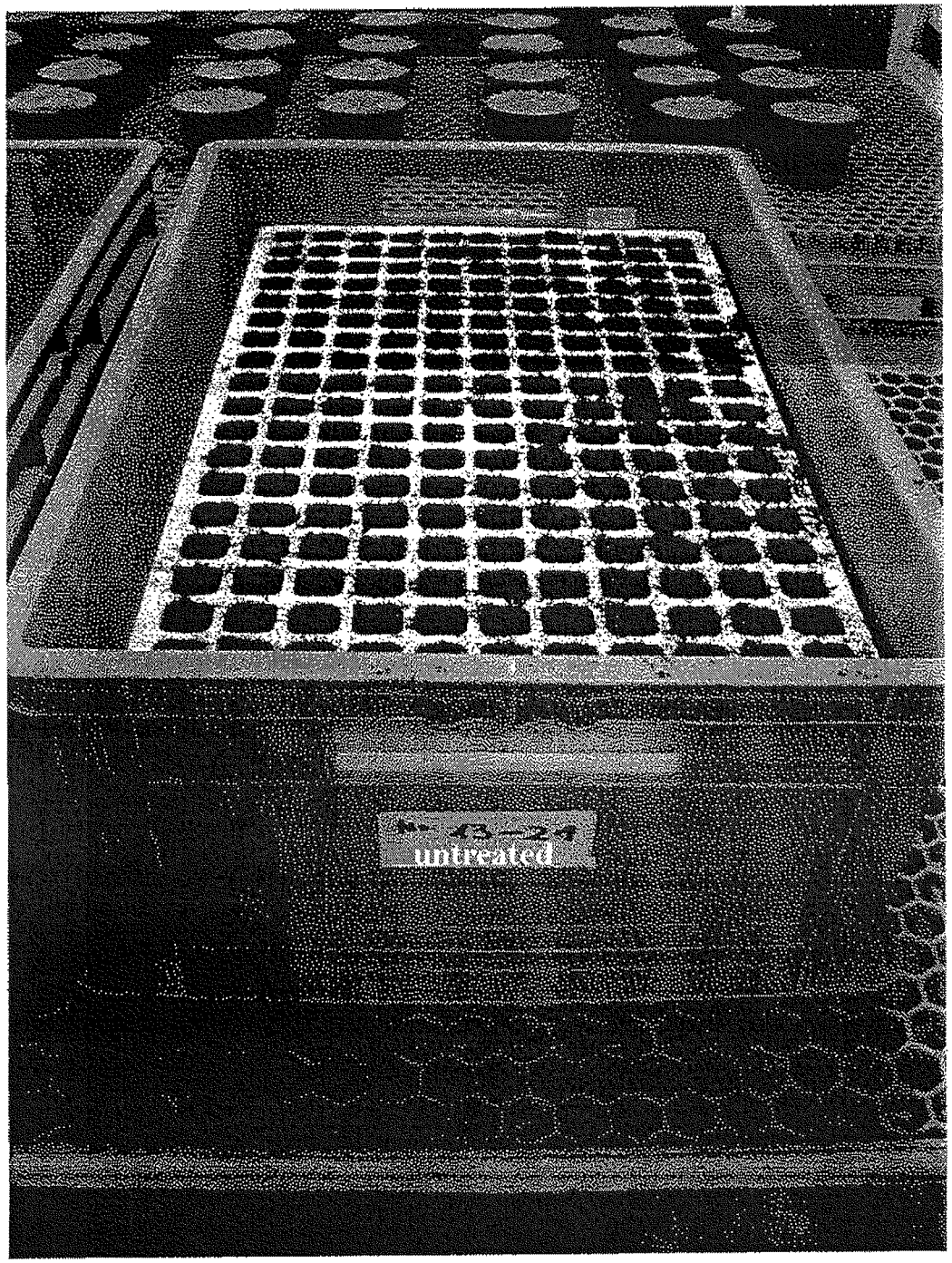
FIG. 2: Floating Box with floating Styropor culture dishes filled with seedling compost and tobacco seeds.
Figure 3:
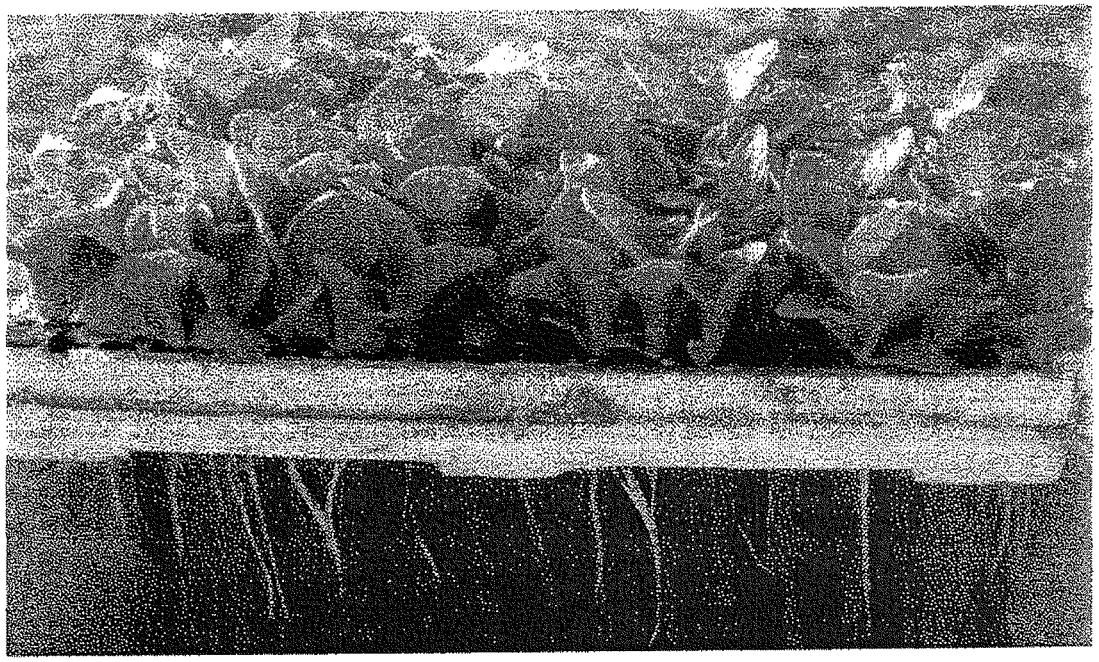
FIG. 3: Styropor culture dishes with tobacco plants after growing in a Floating Box.

The examples which follow describe the invention in detail, but do not limit the present invention in any way.

EXAMPLE 1

Root Growth Test of Tomatoes Under Oxygen Deficiency Conditions in the Nutrient Solution To prepare a suitable solution of the preparation, 1 part by weight of active substance is mixed with water to give the desired concentration.

Tomato seeds (*Solanum lycopersicum* 'Rentita') are grown in rock wool. After germination, the rock wool blocks are transferred into a floating box provided with the solution of the preparation and grown on under suitable climatic conditions.

The nutrient solution of the floating box was not aerated (oxygen deficiency stress).

After the desired period of time, the maximum length of the root per tomato plant is measured, and the average root length per floating box and treatment is calculated.

In this test, it emerged that the compounds according to the invention outperform the control:

TABLE 1

Root growth of tomatoes

| Active substance | Concentration in mg a.i./plant | Length in cm after 4 d |
|---|---|---|
| Compound (I-8) sulfoxaflor | 1.0 | 6.7 |
| Control | | 1.9 |

The invention claimed is:

1. A method for enhancing an intrinsic defense of a plant to abiotic stress factors wherein said method comprises treating a plant in need of said enhancing with the compound N-[6-trifluoromethylpyridin-3-yl]ethyl](methyl)oxido-$\lambda^4$-sulphanylidenecyanamide (I-8).

2. The method according to claim 1, wherein said plant treated with the compound N-[6-trifluoromethylpyridin-3-yl]ethyl](methyl)oxido-$\lambda^4$-sulphanylidenecyanamide (I-8) is transgenic.

3. The method according to claim 1, wherein said plant is in need of protection from abiotic stress factors.

4. The method according to claim 1 wherein the compound N-[6-trifluoromethylpyridin-3-yl]ethyl](methyl)oxido-$\lambda^4$-sulphanylidenecyanamide (I-8) is used in combination with at least one fertilizer.

5. A method for protecting seed or germinating plants: for enhancing an intrinsic defense of a seed or germinating plant to abiotic stress factors, comprising treating a seed or germinating plant in need of said protecting or enhancing with the compound N-[6-trifluoromethylpyridin-3-yl](methyl)oxido-$\lambda^4$-sulphanylidenecyanamide(I-8).

6. The method according to claim 5, wherein the seed or the germinating plant is treated with a nutrient solution in which is present between 0.0005 to 0.025% by weight of the compound N-[6-trifluoromethylpyridin-3-yl]ethyl](methyl)oxido-$\lambda^4$-sulphanylidenecyanamide (I-8) in relation to the total weight of the nutrient solution.

7. The method according to claim 5, wherein said plants are grown in a floating method.

8. A nutrient solution for treating growing plants or germinating plants, comprising an effective amount of the compound N-[6-trifluoromethylpyridin-3-yl]ethyl(methyl)oxido-$\lambda^4$-sulphanylidenecyanamide (I-8) for enhancing an intrinsic defense of a said plant to abiotic stress factors.

9. The nutrient solution according to claim 8, wherein between 0.0005 to 0.025% by weight of the compound N-[6-trifluoromethylpyridin-3-yl]ethyl](methyl)oxido-$\lambda^4$-sulphanylidenecyanamide (I-8) is present in relation to the total weight of the nutrient solution.

10. The method according to claim 1, wherein the plant is treated with a nutrient solution in which between 0.0005 to 0.025% by weight of the compound N-[6-trifluoromethylpyridin-3-yl]ethyl](methyl)oxido-$\lambda^4$-sulphanylidenecyanamide (I-8) is present in relation to the total weight of the nutrient solution.

11. The method according to claim 1, wherein plants are grown from propagation material, comprising seed.

12. The method according to claim 1, wherein PR proteins are induced in growing plants.

13. The method of claim 1, wherein the plant is from the group of: turf; vines; cereals; beet; fruits; legumes; oil crops; cucurbits; fibre plants; citrus fruit; vegetables; Lauraceae; tobacco; nuts; coffee; aubergine; sugarcane; tea; pepper; grapevines; hops; bananas; latex plants and ornamentals.

14. The method according to claim 5, wherein PR proteins are induced in seed or germinating plants.

15. The method of claim 5, wherein the plants are from the group of: turf; vines; cereals; beet; fruits; legumes; oil crops; cucurbits; fibre plants; citrus fruit; vegetables; Lauraceae; tobacco; nuts; coffee; aubergine; sugarcane; tea; pepper; grapevines; hops; bananas; latex plants and ornamentals.

16. The method of claim 13, wherein the plant is chosen from the group consisting of cotton, aubergine, turf, pome fruit, stone fruit, soft fruit, maize, wheat, barley, cucumber, tobacco, vines, rice, cereals, pear, beans, soybeans, oilseed rape, tomato, bell pepper, melons, cabbage, potatoes and apples.

17. The method of claim 15, wherein the plant is chosen from the group consisting of cotton, aubergine, turf, pome fruit, stone fruit, soft fruit, maize, wheat, barley, cucumber, tobacco, vines, rice, cereals, pear, beans, soybeans, oilseed rape, tomato, bell pepper, melons, cabbage, potatoes and apples.

* * * * *